(12) United States Patent
Bohmann et al.

(10) Patent No.: US 7,410,810 B2
(45) Date of Patent: Aug. 12, 2008

(54) ASSAY BASED ON DOPED NANOPARTICLES

(75) Inventors: Kerstin Bohmann, Köln (DE); Werner Hoheisel, Köln (DE); Burkhard Köhler, Leverkusen (DE); Ingmar Dorn, Köln (DE)

(73) Assignee: Bayer Technology Services GmbH, Leverkusen (DE)

( * ) Notice: Subject to any disclaimer, the term of this patent is extended or adjusted under 35 U.S.C. 154(b) by 470 days.

(21) Appl. No.: 10/494,390

(22) PCT Filed: Nov. 4, 2002

(86) PCT No.: PCT/EP02/12256

§ 371 (c)(1),
(2), (4) Date: Apr. 30, 2004

(87) PCT Pub. No.: WO03/040024

PCT Pub. Date: May 15, 2003

(65) Prior Publication Data

US 2005/0064604 A1 Mar. 24, 2005

(30) Foreign Application Priority Data

Nov. 5, 2001 (DE) ................................ 101 53 829

(51) Int. Cl.
*G01N 33/551* (2006.01)
(52) U.S. Cl. .................................................... 436/524
(58) Field of Classification Search ............... 436/514, 436/518, 524–528, 172, 7.92; 435/4, 7.1, 435/7.92

See application file for complete search history.

(56) References Cited

U.S. PATENT DOCUMENTS

| | | | |
|---|---|---|---|
| 3,996,345 A | 12/1976 | Ullman et al. | 424/12 |
| 4,160,016 A | 7/1979 | Ullman | 424/8 |
| 4,174,384 A | 11/1979 | Ullman et al. | 424/8 |
| 4,199,559 A | 4/1980 | Ullman et al. | 424/8 |
| 4,822,733 A | 4/1989 | Morrison | 435/6 |
| 4,996,143 A | 2/1991 | Heller et al. | 435/6 |
| 5,043,265 A | 8/1991 | Tanke et al. | 435/6 |
| 5,210,015 A | 5/1993 | Gelfand et al. | 435/6 |
| 5,279,943 A | 1/1994 | Mathis et al. | 435/7.32 |
| 5,312,728 A | 5/1994 | Lizardi et al. | 435/6 |
| 5,491,084 A | 2/1996 | Chalfie et al. | 435/189 |
| 5,532,129 A | 7/1996 | Heller | 435/6 |
| 5,538,848 A | 7/1996 | Livak et al. | 435/5 |
| 5,565,332 A | 10/1996 | Hoogenboom et al. | 435/69.1 |
| 5,622,821 A | 4/1997 | Selvin et al. | 435/6 |
| 5,625,048 A | 4/1997 | Tsien et al. | 536/23.4 |
| 5,656,433 A | 8/1997 | Selvin et al. | 435/6 |
| 5,674,698 A | 10/1997 | Zarling et al. | 435/7.92 |
| 5,723,591 A | 3/1998 | Livak et al. | 536/22.1 |
| 5,893,999 A | 4/1999 | Tamatani et al. | 252/301.4 R |
| 5,998,146 A | 12/1999 | Latva et al. | 435/6 |
| 6,159,686 A | 12/2000 | Kardos et al. | 435/6 |
| 6,207,392 B1 | 3/2001 | Weiss et al. | 435/7.1 |
| 6,239,271 B1 | 5/2001 | Rabbani et al. | 536/24.3 |
| 6,734,420 B2 * | 5/2004 | Empedocles et al. | 250/271 |
| 6,972,198 B2 * | 12/2005 | Craig et al. | 436/164 |

FOREIGN PATENT DOCUMENTS

| | | |
|---|---|---|
| EP | 0 242 527 | 10/1987 |
| EP | 439 036 | 7/1991 |
| WO | WO 87 07955 | 12/1987 |
| WO | WO 92/01225 | 1/1992 |
| WO | WO 98/43072 | 10/1998 |
| WO | WO 00/29617 | 5/2000 |
| WO | WO 02/44725 A1 | 6/2002 |

OTHER PUBLICATIONS

J.R. Lakowicz, "Principles of Fluorescence Spectroscopy", Kluwer Academic Press, New York, 1999, pp. 368-445.
Yamamoto et al., J. Mol. Biol. 241, 1994, pp. 714-731.
Boisclair et al., J. of Biomolecular Screening, 5, 2000, pp. 319-328.
Heyduk et al., SPIE vol. 3256, 1998, pp. 218-222.
K. Cai et al., J. Biol. Chem. 271, 1996, pp. 27311-27320.
Hochstrasser et al., Biophys. Chem. 45, 1992, pp. 133-141.
Ozaki et al., Nucl. Acids Res. 20, 1992, pp. 5205-5214.
S. Wang et al., Biochemistry 27, 1988, pp. 2033-2039.
Holland et al., Proc. Natl. Acad. Sci USA 88, 1991, pp. 7276-7280.
Lee et al., Nucleic Acids Res. 21, 1993, pp. 3761-3766.
Tyagi and Kramer, Nature Biotechnology 14, 1996, pp. 303-306.
Pollok and Heim, Trends Cell Biol. 9, 1999, pp. 57-60.
Selvin; IEEE J. of Selected Topics in Quantum Electronics 2, 1996, pp. 1077-1087.
Clark et al., Anal. Biochem. 210, 1993, pp. 1-6.
Thomas et al., Proc. Natl Acad. Sci. 75, 1978, pp. 5746 ff.
S.G. Jones et al., Journal of Fluorescence 11, 2001, pp. 13-21.
Tanaka et al., J. Photochem. Photobiol. A 74, 1993, pp. 15 ff.
Marko et al., Biochemistry 31, 1992, pp. 703 ff.
Bawendi et al., and C. Kagan, et al.; Phys. Rev. Lett. 76, 1996, pp. 1517-1520.
O. Schmelz et al., Langmuir 17, 2001, pp. 2861-2865.

(Continued)

*Primary Examiner*—Ann Y Lam
(74) *Attorney, Agent, or Firm*—Norris McLaughlin & Marcus PA

(57) ABSTRACT

The invention relates to an assay based on resonance energy transfer (RET), comprising a first molecule grope A, which is marked with at least one energy donor, and at least one second molecule group B which is marked with at least one energy acceptor, the donor comprising a molecule or particle which can be energetically excited by an external radiation source and which is fluorescence enabled and the acceptor comprising a molecule or particle which can be excited by energy transfer via the donor with partial or complete quenching of the donor fluorescence, and the donor and/or acceptor comprise luminescing inorganic dope nanoparticles having an expansion of $\leq 50$ nanometers, emitting electromagnetic radiation with stokes or anti-stokes scattering after energetic excitation.

58 Claims, No Drawings

OTHER PUBLICATIONS

K. Riwotzki et al, Angewandte Chemie, Int. Ed. 40, 2001, pp. 573-576.

K. Riwotzki, et al, Journal of Physical Chemistry B, vol. 102, 1998, pp. 10129-10135.

H. Meyssamy et al., Advanced Materials, vol. 11, Issue 10, 1999, pp. 840-844.

K. Riwotzki, et al., Journal of Physical Chemistry B. vol. 104, 2000, pp. 2824-2828.

Q. Li, et al., Nanostructured Materials vol. 8, 1999, pp. 825 ff.

M. Yin, et al., Journal of Luminescence, vol. 68, 1996, pp. 335 ff.

Y.H. Li, et al., Nanostructured Materials vol. 11, Issue 3, 1999, pp. 307-310.

Y.L Soo, et al., Journal of Applied Physics vol. 83, Issue 10, 1998, pp. 5404-5409.

R.N. Bhargava, et al, Physical Review Letters vol. 72, 1994, pp. 416-419.

R.N. Bhargava, et al., Journal of Luminescence, vol. 60, 1994, pp. 275 ff.

Ullmann's Encyclopedia of Industrial Chemistry, WILEY-VCH, 6th Edition, 2001 Electronic Release, "The Luminescent Materials: 1. Inorganic Phosphors" chapter.

D. Dexter. J. Chem. Phys. 21, 1953, pp. 836-850.

T. Jüstel et al., Angewandte Chemie, International Edition 37, 1998, pp. 3084-3103.

Niedbala et al., Analytical Biochemistry 293, 2001, pp. 22-30.

Moedritzer and Irani, J. Org. Chem., 1966, 31, p. 1603.

* cited by examiner

SEQUENCE LISTING

```
<160> NUMBER OF SEQ ID NOS: 3

<210> SEQ ID NO 1
<211> LENGTH: 26
<212> TYPE: DNA
<213> ORGANISM: Artificial
<220> FEATURE:
<223> OTHER INFORMATION: Oligonucleotide
<220> FEATURE:
<221> NAME/KEY: modified_base
<222> LOCATION: (1)..(1)
<223> OTHER INFORMATION: The residue at position 1 is modified by a
      thiol group.
<220> FEATURE:
<221> NAME/KEY: modified_base
<222> LOCATION: (26)..(26)
<223> OTHER INFORMATION: The residue at position 26 is modified by a
      dabycl (4-(4-dimethylaminophenylazo)benzoyl) group.

<400> SEQUENCE: 1
ccacgcttgt gggtcaaccc ccgtgg                                          26

<210> SEQ ID NO 2
<211> LENGTH: 17
<212> TYPE: DNA
<213> ORGANISM: Artificial
<220> FEATURE:
<223> OTHER INFORMATION: PCR primer

<400> SEQUENCE: 2
ggccggtggt cgccgcg                                                    17

<210> SEQ ID NO 3
<211> LENGTH: 19
<212> TYPE: DNA
<213> ORGANISM: Artificial
<220> FEATURE:
<223> OTHER INFORMATION: PCR primer

<400> SEQUENCE: 3
acgtgacaga ccgccgggc                                                  19
```

ASSAY BASED ON DOPED NANOPARTICLES

This application is a 371 of PCT/EP02/12256, filed Nov. 4, 2002, and claims priority under 35 USC §119 on the basis of German Application No. 101 53 829.4, filed Nov. 5, 2001.

The present invention relates to a biotechnological assay which is based on a resonance energy transfer (RET) and which can be used to detect biological molecules such as enzymes, antibodies, nucleic acid-binding molecules, nucleic acids, polynucleotides or morpholino.

Immunoassays or nucleic acid detection methods are the basis of many applications in medical diagnosis, in the production control of biotechnologically produced products and in research. One method, which is used here, is that of resonance energy transfer (RET) between dyes.

The principle of resonance energy transfer (RET) is based on radiationless transfer of energy from a donor which is capable of fluorescing to an acceptor which is located in spatial proximity. This technique can be used to determine distances at the molecular level in a range between approx. 1 and 8 nm. The energy which has been transferred to the acceptor can, on the one hand, relax in a radiationless manner by means of internal conversion (RET) and then only leads to the donor fluorescence being quenched. On the other hand, the transferred energy can also be emitted by means of the acceptor fluorescing. This is referred to as fluorescence resonance energy transfer (FRET). These phenomena have been well understood for a long time now and, in the case of a dipole-dipole interaction between donor and acceptor, explained by Förster's theory (see, e.g., J. R. Lakowicz, "Principles of Fluorescence Spectroscopy", Kluwer Academic Press, New York, 1999, pages 368-445). The energy transfer reduces the intensity of the donor fluorescence and its decay time and correspondingly increases the fluorescence of the acceptor or else only excites or sensitizes it for the first time. The efficiency E of the energy transfer is very sensitive to the distance R between the donor and acceptor and declines proportionally to $R_0^6/(R_0^6+R^6)$. The mean range of the energy transfer, at which the efficiency is 50%, is defined by means of a material-specific constant, i.e. the Förster radius $R_0$, and lies in the range of a few nanometers (less than 10 nm). When the excited state of the acceptor relaxes in a radiationless manner it is only donor fluorescence which suffers anything from a reduction through to complete quenching. In that which follows, the term (F)RET is used when the terms RET and FRET can be used alternately. (F)RET-capable donor/acceptor pairs are termed (F)RET pairs. In that which follows, the terms fluorescence and luminescence are used synonymously.

In biological systems, (FRET) is used to detect the spatial proximity to each other of appropriately labeled biomolecules or molecular groups. This method can be used as a method for detecting protein-protein interactions, e.g. as a method for detecting the antigen-antibody reaction in immune reactions, a receptor-ligand interaction, a nucleic acid hybridization or the binding of proteins to nucleic acids. The detection is itself effected by means of measuring the change in the intensity of, or the spectral change in, the donor fluorescence or acceptor fluorescence or by means of measuring a change in the decay time of the donor fluorescence. A large number of applications in this regard are described in the literature, such as the detection of specific antigens in immunofluorescence assays (U.S. Pat. Nos. 3,996,345; 4,160,016; 4,174,384; 4,199,559), the determination of the electrostatic potential in specific, localized regions on the surface of proteins (Yamamoto et al.; J. Mol. Biol. 241, 1994, pages 714-731), or the method involving high-throughput screening (Boisclair et al.; J. of Biomolecular Screening, 5, 2000, pages 319-328).

(F)RET systems are also used to determine absolute distances between two molecules or within a biomolecule. Two labels, which measurably interact in dependence on their distance from each other, are introduced for this purpose. Known applications of this method are the analysis of protein structure or DNA structure (Heyduk et al.; SPIE Vol. 3256, 1998, pages 218-222), the determination of distances within polypeptides (Lakowicz et al.; Biophys. Chem. 36, 1990, pages 99-115), proteins (K. Cai et al.; J. Biol. Chem. 271 1996, pages 27311-27320), polynucleotides (Hochstrasser et al.; Biophys. Chem. 45, 1992, pages 133-141 and Ozaki et al.; Nucl. Acids Res. 20, 1992, pages 5205-5214) or other macromolecules, the investigation of membranes and membrane proteins and their structure (S. Wang et al.; Biochemistry 27, 1988, pages 2033-2039), and the detection (U.S. Pat. Nos. 4,996,143; 5,532,129; 5,565,332) and quantification of nucleic acids which have been amplified by PCR (polymerase chain reaction) (U.S. Pat. Nos. 5,538,848; 5,723,591), e.g. for in vitro diagnosis, genetic analysis, forensics, foodstuff tests, agricultural product tests or parenthood tests. DNA or RNA is detected or quantified directly, i.e. without any additional separation steps.

The 5'-nuclease assay (U.S. Pat. Nos. 5,538,848; 5,210,015; Holland et al.; Proc. Natl. Acad. Sci USA 88, 1991, pages 7276-7280; Lee et al.; Nucleic Acids Res. 21, 1993, pages 3761-3766) which is termed the TaqMan® assay (Applied Biosystems Division of Perkin-Elmer Corp., Foster City, USA) is a quantitative nucleic acid determination by means of real-time PCR which uses (F)RET systems. The method of molecular beacons (Tyagi and Kramer, Nature Biotechnology 14, 1996, pages 303-306; U.S. Pat. No. 5,312,728) is based on a similar mechanism.

Organic dye molecules such as fluorescein, cyanine or rhodamine, for example, are classical, commercially available materials for making efficient (F)RET pairs. A general disadvantage of these organic fluorescent dyes is that they frequently exhibit a stability toward incident light which is inadequate for many applications. Particularly in the presence of oxygen or free radicals, some of them can already be irreversibly damaged or destroyed after a few million light absorption/light emission cycles. Furthermore, the fluorescent organic dye molecules can also have a phototoxic effect on biological material in the vicinity. On the one hand, the broad emission bands of the organic fluorescent dyes, with their additional ramifications into the long-wave region of the spectrum, are unfavorable for simultaneously reading several dyes, i.e. what is termed multiplexing. On the other hand, their usually small Stokes shift, i.e. the difference between the excitation maximum and the emission maximum of a dye and the relatively narrow spectral excitation bands within which an excitation is possible, is disadvantageous. As a result, several light sources and/or elaborate filter systems frequently have to be used, thereby additionally restricting the simultaneous reading of several dyes.

It is also possible to use fluorescent proteins as a FRET pair. In this case, the FRET process involved is also termed a bioluminescence resonance energy transfer (BRET). The fluorescent proteins include the green fluorescent protein GFP (U.S. Pat. No. 5,491,084) and its variants which possess other absorption and/or emission maxima, such as the yellow (YFP) or cyan (CFP) fluorescent proteins (U.S. Pat. No. 5,625,048). In this connection, GFPs can either be used as the donor and acceptor or in combination with other fluorophores such as fluorescein or luciferase (review article: Pollok and Heim; Trends Cell Biol. 9, 1999, pages 57-60). A problem is the small selection of different GFP proteins which satisfy the requirements for a suitable FRET pair (sufficiently large difference in the excitation wavelengths, sufficient overlapping of the donor and acceptor emission and excitation wavelengths). Thus, it has to date only been possible to successfully apply two combinations of GFPs as a FRET pair (review article: Pollok and Heim; Trends Cell Biol. 9, 1999, pages 57-60). Even in combination with other dyes or bioluminescent proteins, the small number and markedly different intensities of the GFPs is a limiting factor.

As an alternative to organic dyes, metal chelates or metal complexes are also used for FRET (see, e.g., Selvin; IEEE J. of Selected Topics in Quantum Electronics 2, 1996, pages 1077-1087).

Lanthanide chelates can be employed either as (F)RET pairs (Clark et al., Anal. Biochem. 210, 1993, pages 1 ff.) or as only the donor which transfers the energy to organic fluorescent dyes (Thomas et al.; Proc. Natl. Acad. Sci. 75, 1978, pages 5746 ff; S. G. Jones et al.; Journal of Fluorescence 11, 2001, pages 13-21) or to quenchers (Tanaka et al.; J. Photochem. Photobiol. A 74, 1993, pages 15 ff; Marko et al.; Biochemistry 31, 1992, pages 703 ff.).

Systems or assays which are based on energy transfer and on fluorochromes and chelates having a long lifetime have been disclosed in a number of patents (WO 8 707 955, EP 242 527, EP 439 036, WO 9201225, U.S. Pat. Nos. 4,822,733, 5,279,943, 5,622,821, 5,656,433, 5,998,146, 6,239,271). They use time gated fluorimetry (TGF) and/or time-resolved fluorimetry (TRF) for detecting an analyte.

In this connection, TGF is understood as being a measurement mode in which the excitation is effected using a pulsed light source (laser, photoflash lamp) and, after a defined delay time which then follows, the light emission is measured within a given time window. The delay time is sufficiently long to detect the long-lived fluorescence of the lanthanide chelates with an adequately high intensity. However, the delay time virtually complete discriminates against the short-lived background fluorescence (usually <1 μs) which is elicited by intrinsic autofluorescence of the biological material, impurities in the solvent or surrounding vessel materials. In contrast to the TGF mode, measurements carried out in the TRF mode measure the fluorescence as a function of time at a fixed wavelength. In this connection, the donor is also excited by a pulsed light source or else by a light source which has been modulated in some other way.

However, a disadvantage of the lanthanide chelates or metal complexes is the fact that their chemical stability is low for a number of applications or that their fluorescence properties depend on the chemical environment of the particles. Frequently, additional separation steps, or an additional complex formation, is/are also required in order to be able to measure a fluorescence.

FRET effects have also been observed in the case of particulate label systems which are based on semiconductor nanocrystals, what are termed quantum dots: (Bawendi et al. and C. Kagan et al.; Phys. Rev. Lett. 76, 1996, pages 1517-1520). Quantum dots are also able to interact with organic fluorophores (O. Schmelz et al.; Langmuir 17, 2001, pages 2861-2865).

It is possible to exploit FRET effects between quantum dots themselves or else between quantum dots and other substances (e.g. dyes). WO 00/29617 discloses that it is possible to detect proteins and nucleic acids using quantum dots as labels. In particular, the patent also discloses their use as fluorophores in the case of the hairpin-like DNA structures known as "molecular beacons".

However, a disadvantage of the quantum dots is that they have to be produced with the highest possible degree of precision. Since the emission wavelength of the fluorescent light depends on the size of the quantum dots, it is necessary to achieve a very narrow particle size distribution in a sample. In order to ensure that the fluorescent light is of the narrow band width which is required for the multiplexing, the differences in size between quantum dots of one species can only be a few Angströms, i.e. amount to only a few monolayers. This places high demands on the synthesis. In addition, due to radiationless electron/hole pair recombinations on their surface, quantum dots normally exhibit relatively weak quantum efficiencies. For this reason, it is necessary to produce core-shell structures (Xiaogang Pent et al.; J. Am. Chem. Soc. 119, 1997, pages 7019-7029), which require a more elaborate synthesis, in order to increase the quantum efficiencies.

Furthermore, in the case of quantum dots, the decay time of the fluorescence is very short and is in the lower nanosecond range. For this reason, it is not possible to make any measurements in the TGF mode and only possible to make measurements in the TRF mode using relatively elaborate technology and equipment. Another disadvantage of the quantum dot systems is their composition, with many of the systems containing toxic elements such as cadmium, selenium or arsenic.

Nano-scale phosphors which are of less than 50 nm in size, and which are designated luminescent inorganic doped nanoparticles (lid nanoparticles) below, have been described many times in scientific publications.

The published lid nanoparticles consist of oxides, sulfides, phosphates or vanadates which are doped with lanthanides or with Mn, Al, Ag or Cu. These lid nanoparticles fluoresce, due to their doping, in a narrow spectral range. The preparation of the following lid nanoparticles has been published, inter alia: $LaPO_4$:Ce,Th; (K. Riwotzki et al.; Angewandte Chemie, Int. Ed. 40, 2001, pages 573-576); $YVO_4$:Eu, $YVO_4$:Sm, $YVO_4$:Dy (K. Riwotzki, M. Haase; Journal of Physical Chemistry B; Vol. 102, 1998, pages 10129-10135); $LaPO_4$:Eu, $LaPO_4$:Ce, $LaPO_4$:Ce,Tb; (H. Meyssamy, K. Riwotzki, A. Kornowski, S. Naused, M. Haase; Advanced Materials, Vol. 11, Issue 10, 1999, pages 840-844); (K. Riwotzki, H. Meyssamy, A. Kornowski, M. Haase; Journal of Physical Chemistry B Vol. 104, 2000, pages 2824-2828); ZnS:Tb, ZnS:$TbF_3$, ZnS:Eu, ZnS:$EuF_3$, (M. Ihara, T. Igarashi, T. Kusunoki, K. Ohno; Society for Information Display, Proceedings 1999, Session 49.3); $Y_2O_3$:Eu (Q. Li, L. Gao, D. S. Yan; Nanostructured Materials Vol. 8, 1999, pages 825 ff); $Y_2SiO_5$:Eu (M. Yin, W. Zhang, S. Xia, J. C. Krupa; Journal of Luminescence, Vol. 68, 1996, pages 335 ff.); $SiO_2$:Dy, $SiO_2$:Al, (Y. H. Li, C. M. Mo, L. D. Zhang, R. C. Liu, Y. S. Liu; Nanostructured Materials Vol. 11, Issue 3, 1999, pages 307-310); $Y_2O_3$:Tb (Y. L. Soo, S. W. Huang, Z. H. Ming, Y. H. Kao, G. C. Smith, E. Goldburt, R. Hodel, B. Kulkarni, J. V. D. Veliadis, R. H. Bhargava; Journal of Applied Physics Vol. 83, Issue 10, 1998, pages 5404-5409); CdS:Mn (R. N. Bhargava, D. Gallagher, X. Hong, A. Nurmikko; Physical Review Letters Vol. 72, 1994, pages 416-419); ZnS:Tb (R. H. Bhargava, D. Gallagher, T. Welker; Journal of Luminescence, Vol. 60, 1994, pages 275 ff.). Ullmann's Encyclopedia of Industrial Chemistry, WILEY-VCH, 6th edition, 2001 Electronic Release, The "Luminescent Materials: 1. Inorganic Phosphors" chapter, provides a review of the known luminescent inorganic doped materials which are of a few micrometers in size, and of their use as industrial phosphors.

In many cases, a (F)RET between a donor (sensitizer) and an acceptor (emitter) is also responsible for the light emission which is elicited in luminous phosphors as are used, for example, for fluorescent lamps (D. Dexter; J. Chem. Phys. 21, 1953, pages 836-850, T. Jüstel et al.; Angewandte Chemie, International Edition 37, 1998, pages: 3084-3103). Since, however, donor and acceptor are present in a shared crystal lattice in the case of a luminescent phosphor, the (F)RET system of the luminescent phosphors cannot be used for detecting a parameter change resulting from a biochemical process.

U.S. Pat. No. 5,043,265 discloses that it is possible to detect biological macromolecules which are coupled to nanoscale luminescent phosphor particles by measuring the fluorescence. The patent explains that the fluorescence of the particles will rapidly lose its intensity as the diameter becomes smaller and that the particles should therefore be larger than 20 nm and preferably even larger than 100 nm.

U.S. Pat. No. 5,674,698 discloses special types of luminous phosphors for use as biological labels. These luminous phosphors are "upconverting phosphors" which have the property of emitting light, whose wavelength is shorter than that of the absorbed light, by way of a two-photon process. Using these particles makes it possible to work almost free of background since such autofluorescence is to a very large extent suppressed. The particles are prepared by milling and then annealing. The particle size is between 10 nm and 3 µm, preferably between 300 nm and 1 µm. These particles are primarily used in immunoassays (see, for example, Niedbala et al.; Analytical Biochemistry 293, 2001, pages 22-30). One disadvantage of these particles is their broad size distribution resulting from the preparation process. Another is that, in the case of the smaller particles, there are frequently qualitative restraints which result from the preparation and which are reflected in the preferred particle size of 300 nm-1 µm. In general, a higher excitation intensity than in the case of the one-photon process is required for exciting a two-photon process in order to achieve comparable emission intensity.

U.S. Pat. No. 6,159,686 discloses special phosphor/dye complexes for carrying out photophysical catalysis or photodynamic therapy. Upconverting phosphors are initially excited with innocuous infrared light. Energy in the visible light range is then transferred to the dye, which in turn, acting as a catalyst, transfers its energy to a target molecule. It is also possible to detect target analytes using such pairs of upconverting phosphors and suitable dyes. For this, a complex composed of target analyte, phosphor and dye is formed in the presence of the target analyte, with this complex then permitting, as a result of the spatial proximity, an energy transfer from the phosphor to the dye. This patent also discloses the use of these upconverting phosphors, together with a corresponding "matched label" in homogeneous, heterogeneous and competitive assays. In this connection, the phosphors can be used either as donor or as acceptor.

The object according to the invention consists in providing an assay for detecting a biological target molecule, which assay does not suffer from the disadvantages described in the prior art.

The object is achieved, according to the invention, by means of an assay which is based on resonance energy transfer (RET) or on fluorescence resonance energy transfer (FRET) and which contains a first molecule group A, which is labeled with at least one energy donor according to the invention, and at least one second molecule group B, which is in each case labeled with at least one energy acceptor.

Within the meaning of the invention, a donor is understood as being a molecule or particle which is energetically excited, continuously or in a time-modulated manner, by an external radiation source (electromagnetic radiation or particle radiation) and which is capable of fluorescence.

Within the meaning of the invention, an acceptor is understood as being a molecule or particle which is excited by energy transfer by way of the donor, which completely or partly quenches donor fluorescence and which can, but which does not have to, itself be capable of fluorescence. A donor which is not capable of fluorescence relaxes in a radiationless manner.

According to the invention, donor and/or acceptor comprise lid nanoparticles which have a breadth of $\leqq 50$ nanometers and which, after an energetic excitation, emit electromagnetic radiation with a Stokes or Antistokes shift.

The advantage of an assay which is based on lid nanoparticles having a breadth of 50 nanometers or less is that the particles exhibit less potential for steric problems or undesirable sedimentation in an assay than can be the case when using larger particles. In addition, the presence of the lid nanoparticle has less influence on the kinetics of a binding reaction (e.g. immune reaction or DNA hybridization) or of a biochemical process which is to be investigated.

In this, larger lid particles suffer from disadvantages when making measurements in the TRF mode. In the case of a (F)RET, it is only possible for energy to be transferred from, for example, a lid particle, which is acting as donor, to a molecule which is located in spatial proximity, and which is acting as acceptor, within a distance extending a few nanometers. This means that, in the case of relatively large particles, a significant part of the particle volume, and consequently of the doping ions in the particle, is not within range of the acceptor which is located in front of the particle surface and is therefore not involved in the (F)RET. As a result, the effect of the decay time change (TRF mode) caused by a (F)RET is less pronounced or possibly no longer measurable. For the same reasons, a complete, or at least significant, quenching of the donor fluorescence by the acceptor would no longer be possible.

A RET or FRET can be effected by means of a dipole/dipole interaction (Förster transfer), by means of an interaction with involvement of higher multipoles, or by means of the migration of charges or excitons. In the case of a Förster transfer, the spectral overlap between the donor emission and the acceptor absorption must be sufficiently large. The distance between the donor and acceptor can consequently be measured since the efficiency of the energy transfer depends on the distance.

Preference is given to at least one of the two partners (donor or acceptor) being a luminescent inorganic doped nanoparticle having a long fluorescence decay time (>5 ns). The other partner in each case either contains a molecular, organic chromophore or a luminescent inorganic doped nanoparticle which preferably exhibits a shorter fluorescence decay time. In this connection, the lid nanoparticle having a long fluorescence decay time has a halflife of more than 5 ns, preferably between 1 µs and 50 ms, and particularly preferably between 100 µs and 10 ms. In an assay of this design, the donor can be excited with a pulsed light source of suitable wavelength. When the donor/acceptor pair are in appropriate spatial proximity to each other (a few nanometers), a FRET can now take place, i.e. the acceptor, e.g. a molecular chromophore, is sensitized and can release its energy by means of light emission. Since the decay time e.g. of the donor fluorescence is very long, the decay time of the sensitized fluorescence of the acceptor is also very long, on account of the FRET, and consequently very much longer than as a result of the direct excitation of the acceptor by the pulsed light source. When the fluorescence is measured in the TGF mode, it is therefore possible, by masking out the short-lived acceptor fluorescence, to detect the sensitized acceptor fluorescence virtually in the absence of background and consequently with a high degree of sensitivity. By using a light source which is modulated with a suitable frequency, it is also possible to carry out phase-sensitive measurements. The donor can also exhibit short-lived fluorescence and the acceptor exhibit long-lived fluorescence, as can be observed, for example, with the system of doped LaPO$_4$ nanoparticles. In this case, those nanoparticles which are doped with Cer ions act as donor and those which are doped with terbium ions act as acceptor.

In another embodiment, the donor consists of a lid nanoparticle and the acceptor consists of a conducting material. These materials can be metals, such as gold (Au), silver (Ag) or platinum (Pt), or conducting oxides, such as indium tin oxide (ITO), or conducting polymers. In this connection, they can be present in particulate form as nanoparticles or microparticles, or consist of a planar surface, which can also be structured.

The lid nanoparticles which are used in the assay according to the invention are doped with foreign ions such that the can be excited by narrow-band or broad-band, pulsed, modulated or continuous electromagnetic radiation with wavelengths in the range of infrared light, of visible light, of UV, of X-ray light or of γ-radiation or particle radiation, such as electron radiation, or by a particle beam, and the acceptor can be qualitatively and/or quantitatively detected by time-resolved or continuous measurement of material-specific fluorescent light or its change.

The biochemical reaction is detected by measuring a RET or FRET, i.e. by measuring the change in the luminescence properties (intensity, spectral or by a change in the decay time) of the lid nanoparticles and/or the other chromophores involved. In this way, it is possible to detect, in an assay, the changes in the spacing of the (F)RET partners involved.

The spatial proximity of an acceptor can be detected, in a (F)RET system, from the change in the donor decay time. Because of the presence of another decay channel, due to the transfer of energy to the acceptor, the decay time of the donor fluorescence is significantly shortened. This change can be measured both in the case of the donor fluorescence and in the case of the sensitized acceptor fluorescence (measurement in the TRF mode). The emission decay time, as an observed quantity for FRET, offers an alternative to measuring intensities. It makes a measurement which is independent of concentration effects, quantum efficiency of the chromophore, incomplete labeling and partial or complete quenching of the acceptor fluorescence. Virtually every photon which is detected is a contribution to the useful signal. In the case of a Förster transfer, and when using the mathematical relationships which are known for this purpose, it is also possible to infer the spatial distance between the donor and the acceptor from the decrease in the decay time of the donor fluorescence. An important advantage of using lid nanoparticles is their intrinsically long decay time, which frequently extends into the range of a few milliseconds and can therefore be conveniently recorded using simple experimental means.

The lid nanoparticles have a virtually spherical morphology, with breadths in the range from 1 nm to 50 nm, preferably in the range from 1 nm to less than 20 μm, and particularly preferably in the range from 2 nm to 10 nm. Breadths are understood as meaning the maximum separation of two points lying on the surface of a lid nanoparticle. The lid nanoparticles can also have an ellipsoidal morphology or be faceted, with breadths which lie within the abovementioned limits.

In addition to this, the lid nanoparticles can also exhibit a pronounced needle-shaped morphology, with a breadth of from 3 nm to 50 nm, preferably of from 3 nm to less than 20 nm, and a length of from 20 nm to 5 μm, preferably of from 20 nm to 500 nm. In this case, breadth is understood as meaning the maximum separation of two points which lie on the surface of a needle-shaped lid nanoparticle and, at the same time, in a plane which is perpendicular to the longitudinal axis of the needle-shaped lid nanoparticle. The particle size can be determined by the method of ultracentrifugation or of gel permeation chromatography or by means of electron microscopy.

Materials which are suitable, within the meaning of the invention, for the lid nanoparticles are inorganic nanocrystals whose crystal lattices (host material) are doped with foreign ions. These materials include, in particular, all the materials and material classes which are used as what are termed phosphors, e.g. in luminescent screens (e.g. for cathode-ray tubes) or as coating material in fluorescent lamps (for gas-discharge lamps), as are mentioned, for example, in Ullmann's Encyclopedia of Industrial Chemistry, WILEY-VCH, 6$^{th}$ edition, 2001 Electronic Release, the "Luminescent Materials: 1. Inorganic Phosphors" chapter, and also the lid nanoparticles which are known from the above-cited prior art. In these materials, the foreign ions serve as activators for the emission of fluorescent light following excitation by UV light, visible light or IR light, X-rays or gamma rays, or electron beams. In the case of some materials, several types of foreign ions are also incorporated into the host lattice in order, on the one hand, to produce activators for the emission and, on the other hand, to make the excitation of the particle system more efficient or in order to adjust the absorption wavelength by shifting it to the wavelength of a given excitation light source (what are termed sensitizers). The incorporation of several types of foreign ions can also be used to select a particular combination of fluorescence bands which are to be emitted by a particle.

The host material of the lid nanoparticles preferably consists of compounds of the type XY. In this connection, X is a cation derived from elements of the main groups 1a, 2a, 3a and 4a, of the subgroups 2b, 3b, 4b, 5b, 6b or 7b, or of the lanthanides, of the periodic system. In some cases, X can also be a combination or mixture of said elements. Y can be a polyatomic anion which contains one or more element(s) of the main groups 3a, 4a or 5a, or of the subgroups 3b, 4b, 5b, 6b, 7b and/or 8b, and also elements of the main groups 6a and/or 7a. However, Y can also be a monoatomic anion from the main group 5a, 6a or 7a of the periodic system. The host material of the lid nanoparticles can also consist of an element from main group 4a of the periodic system. Elements of the main groups 1a and 2a, or from the group containing Al, Cr, Tl, Mn, Ag, Cu, As, Nb, Nd, Ni, Ti, In, Sb, Ga, Si, Pb, Bi, Zn and Co, and/or elements from the lanthanides, can be used as doping. Combinations of two or more of these elements can also be used, in different relative concentrations to each other, as doping material. The concentration of the doping material in the host lattice is between $10^{-5}$ mol % and 50 mol %, preferably between 0.01 mol % and 30 mol %, particularly preferably between 0.1 mol % and 20 mol %. The doping material is selected such that the decay time of the fluorescence which it induces is long (>100 ns).

Sulfides, selenides, sulfoselenides, oxysulfides, borates, aluminates, gallates, silicates, germanates, phosphates, halophosphates, oxides, arsenates, vanadates, niobates, tantalates, sulfates, tungstates, molybdates, alkali metal halides and also other halides, or nitrides, are preferably used as host materials for the lid nanoparticles. Examples of these material classes are cited, together with the corresponding dopings, in the following list (materials of the type B:A, with B=host material and A=doping material):

LiI:Eu; NaI:Tl; CsI:Tl; CsI:Na; LiF:Mg; LiF:Mg,Ti; LiF:Mg,Na; $KMgF_3$:Mn; $Al_2O_3$:Eu; BaFCl:Eu; BaFCl:Sm; BaFBr:Eu; $BaFCl_{0.5}Br_{0.5}$:Sm; $BaY_2F_8$:A (A=Pr, Tm, Er, Ce); $BaSi_2O_5$:Pb; $BaMg_2Al_{16}O_{27}$:Eu; $BaMgAl_{14}P_{23}$:Eu; $BaMgAl_{10}O_{17}$:Eu; $BaMgAl_2O_3$:Eu; $Ba_2P_2O_7$:Ti; $(Ba,Zn,Mg)_3Si_2O_7$:Pb; $Ce(Mg,Ba)Al_{11}O_{19}$; $Ce_{0.65}Tb_{0.35}MgAl_{11}O_{19:Ce,Tb}$; $MgAl_{11}O_{19}Ce,Tb$; $MgF_2$:Mn; $^{MgS:Eu;\ MgS:Ce;\ MgS:Sm;\ MgS:(Sm,Ce);\ (Mg,Ca)S:Eu;}$ $MgSiO_3$:Mn; $3.5MgO.0.5MgF_2.GeO_2$:Mn; $MgWO_4$:Sm; $MgWO_4$:Pb, $6MgO.As_2O_5$:Mn; $(Zn,Mg)F_2$:Mn; $(Zn_4Be)SO_4$:Mn; $Zn_2SiO_4$:Mn; $Zn_2SiO_4$:Mn,As; ZnO:Zn; ZnO:Zn,Si,Ga; $Zn_3(PO_4)_2$:Mn; ZnS:A (A=Ag, Al, Cu); (Zn,Cd)S:Aa (A=Cu, Al, Ag, Ni); $CdBO_4$:Mn; $CaF_2$:Mn; $CaF_2$:Dy; CaS:A (A=lanthanides, Bi); (Ca,Sr)S:Bi; $CaWO_4$:Pb; $CaWO_4$:Sm; $CaSO_4$:A (A=Mn, lanthanides); $3Ca_3(PO_4)_2.Ca(F,Cl)_2$:Sb, $M_n$; $CaSiO_3$:Mn,Pb; $Ca_2Al_2Si_2O_7$:Ce; $(Ca,Mg)SiO_3$:Ce; $(Ca,Mg)SiO_3$:Ti; $2SrO.6(B_2O_3).SrF_2$:Eu; $3Sr_3(PO_4)_2.CaCl_2$:Eu; $A_3(PO_4)_2.ACl_2$:Eu (A=Sr, Ca, Ba); $(Sr,Mg)_2P_2O_7$:Eu; $(Sr,Mg)_3(PO_4)_2$:Sn; SrS:Ce; SrS:Sm,Ce; SrS:Sm; SrS:Eu; SrS:Eu,Sm; SrS:Cu,Ag; $Sr_2P_2O_7$:Sn; $Sr_2P_2O_7$:Eu; $Sr4Al_{14}O_{25}$:Eu; $SrGa_2S_4$:A (A=lanthanides, Pb); $SrGa_2S_4$:Pb; $Sr_3Gd_2Si_6O_{18}$:Pb,Mn; $YF_3$:Yb,Er; $YF_3$:Ln (Ln=lanthanides); $YLiF_4$:Ln (Ln=lanthanides; $Y_3Al_5O_{12}$:Ln (Ln=lanthanides); $YAl_3(BO_4)_3$:Nd,Yb; $(Y,Ga)BO_3$:Eu; $(Y,Gd)BO_3$:Eu; $Y_2Al_3Ga_2O_{12}$:Tb; $Y_2SiO_5$:Ln (Ln=lanthanides); $Y_2O_3$:Ln (Ln=lanthanides); $Y_2O_2S$:Ln (Ln=lanthanides); $YVO_4$:A (A=lanthanides, In); $Y(P,V)O_4$:Eu; $YTaO_4$:Nb; $YAlO_3$:A (A=Pr, Tm, Er, Ce); YOCl:Yb,Er; $LnlPO_4$:Ln2 (Ln1, Ln2=lanthanides or mixtures of lanthanides); $A_x(PO_4)_y$:Ln (A=alkaline earth metal, Ln=lanthanides) $LuVO_4$:Eu; $GdVO_4$:Eu; $Gd_2O_2S$:Tb; $GdMgB_5O_{10}$:Ce,Tb; LaOBr:Tb; $La_2O_2S$:Tb; $LaF_3$:Nd,Ce; $BaYb_2F_8$:Eu; $NaYF_4$:Yb,Er; $NaGdF_4$:Yb,Er; $NaLaF_4$:Yb,Er; $LaF_3$:Yb,Er,Tm; $BaYF_5$:Yb,Er; $Ga_2O_3$:Dy; GaN:A (A=Pr, Eu, Er, Tm); $Bi_4Ge_3O_{12}$; $LiNbO_3$:Nd,Yb; $LiNbO_3$:Er; $LiCaAlF_6$:Ce; $LiSrAlF_6$:Ce; $LiLuF_4$:A (A=Pr, Tm, Er, Ce); $Li_2B_4O_7$:Mn, $SiO_x$:Er,Al ($0 \leq x \leq 2$).

The following materials are particularly preferably used as lid nanoparticles: $YVO_4$:Eu, $YVO_4$:Sm, $YVO_4$:Dy, $LaPO_4$:Eu, $LaPO_4$:Ce, $LaPO_4$:Tb, $LaPO_4$:Ce,Th, $LaPO_4$:Ce,Sm, $LaPO_4$:Ce,Dy, $LaPO_4$:Ce,Nd, ZnS:Tb, $ZnS:TbF_3$, ZnS:Eu, $ZnS:EuF_3$, $Y_2O_3$:Eu, $Y_2O_2S$:Eu, $Y_2SiO_5$:Eu, $SiO_2$:Dy, $SiO_2$:Al, $Y_2O_3$:Tb, CdS:Mn, ZnS:Tb, ZnS:Ag, ZnS:Cu. Those particularly preferred materials whose host lattice has a cubic structure are selected, in particular, since, in the case of these materials, the number of individual fluorescence bands reaches a minimum. Examples of these materials are: $MgF_2$:Mn; ZnS:Mn, ZnS:Ag, ZnS:Cu, $^{CaSiO3:Ln,}$ CaS:Ln, CaO:Ln, ZnS:Ln, $Y_2O_3$:Ln, or $MgF_2$:Ln (Ln=lanthanides).

The surface of the lid nanoparticles which are used in accordance with the invention is prepared in such a way that it is possible to couple affinity molecules to this prepared surface. In the assay according to the invention, the affinity molecule enters into interaction with target molecules. Examples of affinity molecules are, e.g., proteins, peptides or oligonucleotides or other nucleic acid molecules or nucleic acid-like molecules, such as PNAs or morpholinos, or oligosaccharides or polysaccharides or haptens, such as biotin or digoxin, or low molecular weight synthetic or natural antigens or epitopes.

The preparation of the surface of the lid nanoparticles can consist in the surface of the lid nanoparticles being modified chemically and/or exhibiting reactive groups and/or connecting molecules which are bound covalently or noncovalently. The connecting molecules which are bound to the surface of the lid nanoparticles can also possess reactive groups.

These reactive groups, which can be charged, uncharged or provided with partial charges, can be either on the surface of the lid nanoparticles or be a part of the connecting molecules. Possible reactive functional groups can be amino groups, carboxylic acid groups, thiols, thioethers, disulfides, imidazoles, guanidines, hydroxyl groups, indoles, vicinal diols, aldehydes, alpha-haloacetyl groups, N-maleimides, mercurides, aryl halides, acid anhydrides, isocyanates, isothiocyanates, sulfonyl halides, imidoesters, diazoacetates, diazonium salts, 1,2-diketones, alpha-beta-unsaturated carbonyl compounds, phosphonic acids, phosphoric esters, sulfonic acids or azolides, or derivatives of said groups.

Examples of connecting molecules which may be mentioned here are phosphonic acid derivatives, ethylene glycol, primary alcohols, amine derivatives, polymers or copolymers, polymerizable coupling agents, silica shells and catenate molecules having a polarity which is opposite to that of the surface of the lid nanoparticles.

It is also possible to use nucleic acid molecules as connecting molecules. They form the connection to an affinity molecule which, for its part, contains nucleic acid molecules possessing sequences which are complementary to the connecting molecules.

An affinity molecule can be bound to connecting molecules covalently or noncovalently using standard methods of organic chemistry such as oxidation, halogenation, alkylation, acylation, addition, substitution or amidation of the adsorbed or adsorbable material. These methods for binding an affinity molecule to the covalently bound or noncovalently bound connecting molecule can be employed before adsorbing the connecting molecule to the lid nanoparticle or after the connecting molecule has already been adsorbed to the lid nanoparticle. It is also possible to bind affinity molecules directly, by incubation, to appropriately treated (e.g. with trimethylsilyl bromide) lid nanoparticles, which, as a result of the treatment, possess a surface which has been altered (e.g. more highly charged, polar).

The molecule groups A and B, which are labeled with donor or acceptor, can be constituents of one and the same molecule and can couple, for example, to the same affinity molecule. A change in the spatial separation of the two molecule groups can be brought about by a change in conformation or by the molecule being cleaved. This change in conformation or cleavage of the molecule can be the result of an interaction of the shared affinity molecule with a target molecule.

The molecule groups A and B can also be located on different molecules, with the molecule groups A and B in each case being coupled to their own affinity molecules.

A spatial change in separation can be brought about by an interaction of the affinity molecules assigned to the molecule groups A and B with a common target molecule or with each other. Such an interaction can, by way of example, comprise an interaction between proteins, e.g. an immune reaction of antigen and antibody, a hybridization of nucleic acids or the interaction between nucleic acids and proteins.

The assay according to the invention can, for example, be a homogeneous immunoassay for detecting an analyte (monoclonal or polyclonal antibody, protein, peptide, oligonucleotide, nucleic acid, oligosaccharide, polysaccharide, hapten or low molecular weight synthetic or natural antigen) in a body sample (such as smears, sputum, organ punctates, biopsies, secretions, spinal fluid, bile, blood, lymphatic fluid, urine or feces). In homogeneous assays, no washing or separating steps are required.

The assay according to the invention can also be a heterogeneous assay.

The assay according to the invention can be employed in solution or in solid phase-supported or array-based systems in which oligonucleotide or polynucleotide strands or antibodies or antigens are immobilized on a surface.

There are various groups of applications for the assay according to the invention.

For one group of applications, the (F)RET partners are located on the same molecule; this means that both (F)RET partners are bound to the same affinity molecule by way of appropriate connecting molecules. The binding of a target molecule to the affinity molecule induces a change in the conformation of the affinity molecule, leading to a spatial change in the labels and consequently to a measurable difference in the (F)RET between them.

For other applications, the (F)RET partners are located on separate molecules and each is coupled to its own affinity molecule. The respective affinity molecules can be selected such that the donor and acceptor interact, with this interaction being produced or terminated by the reaction with the target molecule, thereby inducing a change in the energy transfer.

As an example of a homogeneous kinase assay using (F)RET partners on the same molecule, a lid nanoparticle and a chromophore are connected by a peptide sequence. The peptide sequence contains a kinase-specific recognition sequence. If the peptide sequence is phosphorylated at this site by the kinase, the presence of the phosphate alters the conformation of the peptide sequence and thereby alters, in a measurable manner, the interaction between the (F)RET partners lid nanoparticle and the chromophore.

As an example of a homogeneous immunoassay using (F)RET partners on one molecule in which protein-protein interactions are detected, with antigen-antibody reactions only representing one example of this, a lid nanoparticle and a chromophore are linked by a peptide sequence. The peptide sequence contains an epitope. If an antibody, which specifically recognizes this epitope, binds to the epitope, this then alters the conformation of the peptide sequence and thereby alters, in a measurable manner, the interaction between the (F)RET partners lid nanoparticle and a chromophore.

While the molecule to be detected can bind directly to the affinity molecule, as described above, it can also be indirectly responsible for a molecule binding to the affinity molecule. An example of this would be that of measuring $Ca^{2+}$ concentrations in living cells. For this, use is made of the calcium-dependent binding of calmodulin to the myosin light-chain kinase (MLCK) in smooth muscles. The calmodulin-binding domain of MLCK acts as an affinity molecule and is linked to the (F)RET partners. Depending on the $Ca^{2+}$ concentration, calmodulin binds to the binding domain and brings about a change in the conformation of the detection probe and leads to a change in the measurable (F)RET.

As an example of a competitive immunoassay using (F)RET partners on one molecule, which assay can be employed to detect the concentration of an analyte in a body sample, a lid nanoparticle and a chromophore are linked by a connecting molecule which contains the epitope. The epitope is modelled on an epitope of the analyte to be detected. An affinity molecule binds specifically to the epitope. Adding a sample (e.g. body sample) which contains the analyte to be detected displaces the affinity molecule, which is bound to the epitope, from the epitope, resulting in a change in the conformation of the molecule and, as a result, a measurable change in the interaction between the (F)RET partners lid nanoparticle and the chromophore. This change in the (F)RET is used to determine the concentration of the analyte.

As an example of a homogeneous saturation immunoassay using (F)RET partners on separate molecules, the affinity molecules of the lid nanoparticle and the chromophore are able to recognize different epitopes of the same target molecule, such that the presence of the target molecule results in a measurable energy transfer.

The detection of hCG (human chorionic gonadotrophin) in serum may be mentioned here as an example of a homogeneous immunoassay in which donor and acceptor are located on separate molecules. In this assay, donor and acceptor are coupled to antibodies which recognize different hCG epitopes. If hCG is present in a body sample, both donor and acceptor probes bind to the analyte. A calibration curve can be used to translate the measurable FRET into a concentration of the analyte in the body sample.

As an example of a homogeneous, competitive immunoassay using (F)RET partners and on separate molecules, one or more chromophores are linked to a molecule, which corresponds to parts of, or completely to, the molecule to be detected. A lid nanoparticle is coupled to an affinity molecule which interacts specifically both with the molecule and with the molecule to be detected. Binding occurs between the molecules, resulting in a (F)RET. If a sample (e.g. body sample) containing the molecule to be measured is now added, a displacement reaction takes place depending on the concentration, in said sample, of the molecule to be detected. This leads to a measurable change, in this case to a decrease, in the (F)RET, and a calibration curve can be used to determine the concentration of the molecule to be detected.

As an example of a homogeneous assay using (F)RET partners on one molecule, a lid nanoparticle and a chromophore are linked by a peptide as an affinity molecule. This peptide can be cleaved by an enzyme to be detected. Following cleavage, no (F)RET any longer takes place.

An assay of this type can be used for detecting a particular enzyme activity, for example a protease which is specific for the HI virus, within a sample or cell, with the two (F)RET partners being linked by the short recognition sequence of this protease and being spatially separated from each other by the activity of the protease, namely cleavage of the peptide. The enzyme activity to be detected can also be a restriction endonuclease. In this case, the two (F)RET partners are linked by a nucleic acid.

As an example, the inventive assay can be conducted in accordance with the molecular beacon method. Molecular beacons are DNA molecules which are able to fold, by means of intramolecular complementary sequences, into what is termed a stem loop or hairpin structure. A lid nanoparticle is coupled to one end of the DNA sequence while a chromophore is located, as fluorescence quencher, at the other end. In the hairpin structure, the two (F)RET partners and are arranged closely adjacent to each other and the fluorescence of the donor is therefore completely quenched. The target molecule to be detected possesses sequences which are complementary to the loop region of the DNA sequence. Since binding to the target molecule is energetically more favorable, the hairpin conformation dissociates, chromophore and lid nanoparticle become detached from each other and fluorescence is measurably emitted since (F)RET no longer causes any fluorescence quenching. The hybridization properties can be adjusted such that just one single base mismatch between the molecular beacon and the target DNA results in the hairpin structure not being open. As a result, it is even possible to detect single base differences (e.g. SNPs, single nucleotide polymorphisms).

EXAMPLES OF LINKING OF LID NANOPARTICLES TO ORGANIC MOLECULES

Example 1

Binding Phosphonic Acid Derivatives

The surface of the lid nanoparticle can be chemically modified, for example, by binding on phosphonic acid derivatives which possess functional reactive groups. In this case, phosphonic acid derivatives or phosphonic ester derivatives, such as imino-bis(methylenephosphono)carboxylic acid (can be prepared, for example, by means of the Mannich-Moedritzer reaction, Moedritzer and Irani, J. Org. Chem., 1966, 31, 1603) are bound stably to the surface of the lid nanoparticles. This binding can take place on untreated lid nanoparticles or on lid nanoparticles which have been previously treated (e.g. with trimethylsilyl bromide). Possible reactive functional groups which these phosphonic acid-containing or phosphonic ester-containing connecting molecules carry can be amino groups, carboxylic acid groups, thiols, thioethers, disulfides, imidazoles, guanidines, hydroxyl groups, indoles, vicinal diols, anhydrides, isocyanates, isothiocyanates, sulfonyl halides, imidoesters, diazoacetates, diazonium salts, 1,2-diketones, alpha-beta-unsaturated carbonyl compounds, phosphonic acids, phosphoric esters, sulfonic acids or azoles, or derivatives of said groups.

Example 2

Binding of Ethylene Glycol, Primary Alcohols and Primary Amine Derivatives

Another example of treating the surface of the lid nanoparticles is that of heating the particles in ethylene glycol, with the ethylene glycol being stably bound on the lid nanoparticles while the alkyl chains are eliminated. This treatment results in the particles becoming water-soluble. It is possible to use primary alcohols possessing functionally reactive groups, as cited above, in an analogous manner. In a similar way, primary amine derivatives can also be stably bound to the surface of the lid nanoparticles. The amine derivatives can contain the above-cited reactive functional groups in addition to the amine group.

Example 3

Coating with Silica, Polymers or Copolymers and Polymerizable Coupling Agents

The coating of a lid nanoparticle, or of a group of lid nanoparticles, with silica may be mentioned as another example of chemically modifying the surface of the lid nanoparticle: silica enables the nanoparticles to be conjugated in a simple chemical manner to organic molecules since silica reacts very readily with organic linkers such as triethoxysilanes or chlorosilanes. Another example of a chemical modification is that of coating a lid nanoparticle, or a group of lid nanoparticles, with polymers or copolymers. N-(3-Aminopropyl)-3-mercaptobenzamidines, 3-(trimethoxysilyl)propyl hydrazide and 3-(trimethoxysilyl)propylmaleimide may be mentioned as examples of polymerizable coupling agents. It is also possible to use a multiplicity of different polymerizable coupling agents together for the purpose of providing one or more lid nanoparticles with a coating layer. This can be of particular advantage in the case of coupling agents which only bind weakly to the lid nanoparticle. Examples of coupling agents which are able to form such networks, as the coating for one or more lid nanoparticles, are diacetylenes, styrenebutadienes, vinyl acetate, acrylates, acrylamides, vinyls, styrenes, silicone oxides, boron oxides, phosphorus oxides, borates, pyrroles, polypyrroles and phosphates, and also polymers of at least some of said agents.

Example 4

Surface Modification Using Oxychlorides, and also Noncovalent Linkages Using Catenate Molecules and Amphiphilic Reagents Another option for preparing the surface of the lid nanoparticles is that of using chlorine gas, or organic chlorinating agents, to convert the oxidic transition metal compounds, of which the lid nanoparticles consist, into the corresponding oxychlorides. These oxychlorides themselves react with nucleophiles, such as amino groups, with the formation of transition metal nitrogen compounds. In this way, it is possible, for example, to achieve direct conjugation of proteins via the amino groups of lysine side chains. Conjugating to proteins, after the surface modification with oxychlorides, can also be effected by using a bifunctional linker such as maleimidopropionic acid hydrazide.

In this connection, catenate molecules having a polarity or charge which is opposite to that of the surface of the lid nanoparticle are particularly suitable for noncovalent linkages. Examples of connecting molecules which are linked noncovalently to the lid nanoparticles, and which may be mentioned, are anionic, cationic or zwitterionic detergents, acid or basic proteins, polyamines, polyamides, polysulfonic acids and polycarboxylic acids. It is possible to create a linkage by means of hydrophobic interaction between the lid nanoparticles and amphiphilic reagents which carry a functional reactive group. Chain molecules which have an amphiphilic character, such as phospholipids or derivatized polysaccharides, which can be crosslinked to each other are particularly suitable for this purpose. These molecules can be adsorbed on the surface of the lid nanoparticle by means of coincubation.

Example 5

Using a Connecting Molecule to Bind Affinity Molecules to Lid Nanoparticles

In general, it is possible to use the same affinity molecules as those which are also employed in the case of the fluorescent organic dye molecules which are described in the prior art for specifically binding these latter molecules to the biological, or other organic, substance which is to be detected. An affinity molecule can be a monoclonal or polyclonal antibody, a different protein, a peptide, an oligonucleotide, a plasmid or another nucleic acid molecule, a peptide nucleic acid (PNA) or a morpholino, an oligosaccharide, a polysaccharide, or a hapten, such as biotin or digoxin, or a low molecular weight synthetic or natural antigen. A list of these molecules are published in the generally available literature, e.g. in the "Handbook of Fluorescent Probes and Research Chemicals" ($8^{th}$ edition, 2001, CD-ROM) by R. P. Hauglund, Molecular Probes, Inc.

Reactive groups on the surface of the affinity molecule are used for binding affinity molecules covalently or noncovalently to the lid nanoparticles using a connecting molecule. In this connection, reactive groups on the surface of the affinity molecule are amino groups, carboxylic acid groups, thiols, thioethers, disulfides, imidazoles, guanidines, hydroxyl groups, indoles, vicinal diols, aldehydes, alpha-haloacetyl groups, N-maleimides, mercurides, aryl halides, acid anhydrides, isocyanates, isothiocyanates, sulfonyl halides, imidoesters, diazoacetates, diazonium salts, 1,2-diketones, alpha-beta-unsaturated carbonyl compounds, phosphonic acids, phosphoric esters, sulfonic acids or azolides, or derivatives of said groups. On the surface of the lid nanoparticles, it is possible to use the functional reactive groups, which were described earlier on, of the connecting molecules for conjugating the affinity molecule. Protocols for effecting couplings to reactive groups are described in the generally available literature, e.g. in "Bioconjugate Techniques" (by Greg T. Hermanson, Academic Press 1996).

If donor and acceptor are present on the same molecule, the affinity molecule, which is coupled to the donor by way of one or more connecting molecules, can be bound covalently or noncovalently to the acceptor. Chromophores whose excitation wavelength overlap with the emission wavelength of the respective donor can be used as acceptor. Acceptors can, for example, be lid nanoparticles, organic dyes (e.g. fluorescein, rhodamine, cyanines), organic pigments (e.g. perylenes) or conducting materials (e.g. metals, doped oxides, conducting polymers). These materials can either be present as particular systems or as a planar or structured surface or surface coating. The coupling can take place by way of reactive groups on the affinity molecule and/or the acceptor molecule.

In addition to affinity molecules being linked covalently, it is also possible to produce noncovalent, self-organized compounds. One possibility which may be mentioned in this context is the linking of simple detection probes to avidine-coupled or streptavidine-coupled affinity molecules using biotin as the connecting molecule.

Example 6

Preparing Lid Nanoparticles Composed of $YVO_4$:Eu

The first step consists in preparing $YVO_4$:Eu. $YVO_4$:Eu can be prepared using the method given in K. Riwotzki, M. Haase; Journal of Physical Chemistry B; Vol. 102, 1998, page 10130, left-hand column: 3.413 g of $Y(NO_3)_3.6H_2O$ (8.9 mmol) and 0.209 g of $Eu(NO_3)_3.6H_2O$ (0.47 mmol) are dissolved in 30 ml of distilled water in a Teflon receptacle. 2.73 g of $Na_3(VO_4).10H_2O$, dissolved in 30 ml of distilled water, are added to this solution, while stirring. After a further 20 min of stirring, the Teflon receptacle is placed in an autoclave and heated at 200° C. while continuing to be stirred. After 1 h, the dispersion is removed from the autoclave and centrifuged at 3000 g for 10 min, and the supernatant is discarded. The precipitate is taken up in 40 ml of distilled water. 3.220 g of an aqueous solution of 1-hydroxyethane-1,1-diphosphonic acid (60% by weight) (9.38 mmol) are added to the dispersion. In order to remove $Y(OH)_3$, which has formed from excess yttrium ions, the pH is adjusted to 0.3 with $HNO_3$ and the mixture is stirred for 1 h. Colloidal $V_2O_5$, which becomes apparent as a result of the solution assuming a reddish color, is formed in this connection. After that, the pH is adjusted to 12.5 with NaOH and the mixture is stirred overnight in a closed receptacle. The resulting white dispersion is then centrifuged at 3000 g for 10 min and the supernatant, together with its by-products, is removed. The precipitate consists of $YVO_4$:Eu and can be taken up in 40 ml of distilled water.

In order to isolate the nanoparticles, which are smaller than approx. 30 nm, the dispersion is centrifuged at 3000 g for 10 min, after which the supernatant is decanted and kept on one side. The precipitate is then taken up once again in 40 ml of distilled water and this mixture is centrifuged at 3000 g for 10 min, after which the supernatant is decanted. This supernatant, and the supernatant which is kept on one side, are combined and centrifuged at 60 000 g for 10 min. The supernatant resulting from this centrifugation contains the desired particles. A colloidal solution, from which a redispersible powder can be isolated by drying with a rotary evaporator (50° C.), is obtained after a further step of dialysis against the distilled water (dialysis tubing from Serva, Heidelberg, MWCO 12-14 kD).

Example 7

Preparing Lid Nanoparticles Composed of $LaPO_4$:$Eu^{3+}$

The first step consists in preparing $LaPO_4$:Eu. $LaPO_4$:Eu can be prepared using the method given in H. Meyssamy, K. Riwotzki, A. Kornowski, S. Naused, M. Haase; Advanced Materials, Vol. 11, Issue 10, 1999, bottom of right-hand column on page 843 to top of left-hand column on page 844: 12.34 g of $La(NO_3)_3.6H_2O$ (28.5 mmol) and 0.642 g of $Eu(NO_3)_3.5H_2O$ (1.5 mmol) are dissolved in 50 ml of distilled water and added to 100 ml of NaOH (1 M) in a Teflon receptacle. A solution of 3.56 g $(NH_4)_2HPO_4$ (27 mmol) in 100 ml of distilled water is added to this mixture while stirring. The solution is adjusted to pH 12.5 with NaOH (4 M) and then heated at 200° C. for 2 h in an autoclave while being stirred vigorously. The dispersion is then centrifuged at 3150 g for 10 min and the supernatant is removed. In order to remove unwanted $La(OH)_3$, the precipitate is dispersed in $HNO_3$ (1M) and stirred for 3 days (pH 1). After that, the dispersion is centrifuged (3150 g, 5 min) and the supernatant is removed. 40 ml of distilled water are added to the centrifugate while stirring.

The milky dispersion still contains a broad size distribution. In order to isolate the nanoparticles which are smaller than approx. 30 nm, appropriate centrifugation and decantation steps are subsequently performed in complete analogy with Example 6.

Example 8

Preparing Lid Nanoparticles Composed of $LaPO_4$:Ce, Tb

The first step consists in preparing $LaPO_4$:Ce,Tb. 300 ml of trisethylhexyl phosphate are degassed with a dry stream of nitrogen gas. 7.43 g of $LaCl_3.7H_2O$ (20 mmol), 8.38 g of $CeCl_3.7H_2O$ (22.5 mmol) and 2.8 g of $TbCl_3.6H_2O$ (7.5 mmol) are then dissolved in 100 ml of methanol and added. After that, water and methanol are distilled off in vacuo by heating the solution to from 30° C. to 40° C. A freshly prepared solution consisting of 4.9 g of dry orthophosphoric acid (50 mmol), which have been dissolved in a mixture of 65.5 ml of trioctylamine (150 mmol) and 150 ml of trisethylhexyl phosphate, are then added. The clear solution has to be rapidly placed in a vessel which can be evacuated, and flushed with a stream of nitrogen gas, in order to minimize the oxidation of $Ce^{3+}$ when the temperature is raised. The solution is subsequently heated at 200° C. During the heating phase, some of the phosphoric acid ester groups are cleaved, leading to a gradual lowering of the boiling point. The heating phase is terminated when the temperature falls to 175° C. (from approx. 30 to 40 h). After the solution has cooled down to room temperature, a 4-fold excess of methanol is added, leading to the nanoparticles precipitating out. The precipitate is separated off, washed with methanol and dried.

Example 9

Preparing Lid Nanoparticles Composed of LaPO$_4$:Eu$^{3+}$ 490 mg (5.0 mmol) of dry orthophosphoric acid and 6.5 ml (15 mmol) of trioctylamine are dissolved in 30 ml of trisethylhexyl phosphate. 1.76 g of La(NO$_3$)$_3$.7H$_2$O (4.75 mmol) and 92 mg of EuCl$_3$.6H$_2$O (0.25 mmol) are then dissolved in 50 ml of trisethylhexyl phosphate and this solution is combined with the first solution. The resulting solution is degassed in vacuo and then heated at 200° C. for 16 h under nitrogen. During the heating phase, some of the phosphoric acid ester groups are cleaved, leading to a gradual lowering of the boiling point. The heating phase is terminated when the temperature falls to 180° C. After the solution has cooled down to room temperature, methanol is added, leading to the nanoparticles precipitating out. The precipitate is separated off using a centrifuge, washed twice with methanol and dried.

Example 10

Dissolving the Nanoparticles Prepared in Example 8 in Water by the Reaction of Ethylene Glycol or Polyethylene Glycol 50 mg of the LaPO$_4$:Ce,Tb nanoparticles (~140 nmol) prepared in Example 8 are heated, at 210° C. for 3 hrs and while stirring and under an inert gas, with 5 ml of ethylene glycol (~180 mmol) (as an alternative, it is also possible to use other alcohols, in particular diols, preferably polyethylene glycols of differing chain length, HO—(CH$_2$—CH$_2$—O)$_n$—OH, where n=2-9) and 5 µl of sulfuric acid (96-98%). The particles go into solution at approx. 135° C. A water jet vacuum of approx. 1.5 mbar is then applied and about half the ethylene glycol is distilled off; the residue remains clear. The residue is then dialyzed against water overnight (Spectra/Por dialysis tubing, 5-6,000 MWCO, Spektrum, Netherlands).

Example 11

Using Oxidation to Carboxyl-functionalize Nanoparticles Prepared in Example 10

0.5 ml of 96-98% strength sulfuric acid is first of all added, while stirring, to 100 mg (~300 nmol) of the nanoparticles prepared in Example 10 in 20 ml of water. 1 mM KMnO$_4$ solution is added dropwise until there is no further decoloration of the violet color. The same quantity of KMnO$_4$ solution is then added once again and the mixture is left to stir overnight (>12 h) at room temperature. Excess permanganate is reduced by adding freshly prepared 1 mM sodium sulfite solution dropwise. The mixture is dialyzed overnight against 0.1M MES, 0.5M NaCl, pH 6.0 (Spectra/Por dialysis tubing, 5-6,000 MWCO, Spektrum, Netherlands).

Example 12

Removing the Alkyl Chains of the Trisethylhexyl Phosphate from the Surface of the Nanoparticles Described in Example 8 by Means of Reaction with Bromotrimethylsilane 300 mg of the LaPO$_4$:Ce,Tb nanoparticles (~850 nmol) prepared in Example 8 are boiled, under reflux for 4 hours, with 2.3 g (15 mmol) of bromotrimethylsilane in 100 ml of chloroform; most of the bromotrimethylsilane excess, and the intermediate which is formed, are distilled off and hydrolysis with a low concentration of ammonia subsequently takes place. For this, 100 µl of 25% strength ammonia are added to 6 ml of water and stirring takes place at RT overnight. The particles are present in a milky emulsion, and a portion of them sedimented out after several hours.

Example 13

Coupling the Nanoparticles Prepared in Example 12 to 11-bis-(phosphorylmethyl)aminoundecanoic acid and 1,4-bis(3-aminopropoxy)butane In order to prepare 11-bis(phosphorylmethyl)aminoundecanoic acid, 201 g of 11-aminoundecanoic acid, 170 g of phosphorous acid, 200 ml of concentrated hydrochloric acid and 200 ml of water are initially introduced and heated to 100° C. 324 g of formalin (37%) are then added dropwise within the space of 1 h and the mixture is subsequently stirred at 100° C. for a further 1 h. After the mixture has cooled down to room temperature, the product is filtered off with suction and dried in vacuo. This results in 334 g of 11-bis(phosphorylmethyl)aminoundecanoic acid, which was characterized by means of elemental analysis (C,H,N,P).

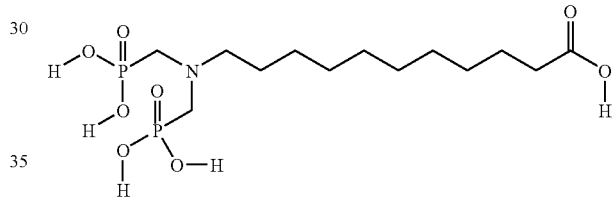

As an alternative, it is possible to use molecules of the following formula, where the radical (R) is an alkylene having from 1 to 17 carbon atoms, preferably 3-12 carbon atoms, or an alkylenearylene radical having 7-12 carbon atoms:

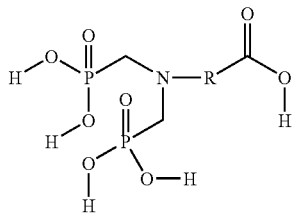

0.894 g (4.375 mmol) of 1,4-bis(3-aminopropoxy)butane is added to 0.5 g (1.85 mmol) of 11-bis(phosphorylmethyl) aminoundecanoic acid in 2 ml of ethylene glycol. After a clear solution has formed (exothermic reaction), 35 mg (=100 nmol) of the nanoparticles prepared in Example 12 are added at approx. 50° C. and the mixture is heated to 125° C. The particles go into solution completely at 120° C. After 4 hrs, a clear light brown solution is present, with this solution also remaining clear after it has cooled down to RT. It is dialyzed overnight against 2×2 l of 10 mM Na carbonate buffer, pH 8.5 (Spectra/Por dialysis tubing, 5-6,000 MWCO, Spektrum, Netherlands). The dialysate is clear.

Example 14

Biotinylating Nanoparticles Prepared in Example 13

6.2 ml (=5 mg or ~15 nmol) of the particles prepared in Example 13 are inspissated on a rotary evaporator and concentrated down to 4.81 mg/ml. The particles are incubated, at RT for 4 hrs and while being rotated, with a 20-fold molar excess of biotin-X-NHS (sulfobiotin-aminocaproic acid-N-hydroxysuccinimide ester, Calbiochem, Schwalbach), which is dissolved in water, and then dialyzed against PBS buffer (8 mM $K_2HPO_4$; 150 mM NaCl; 2 mM $Na_2HPO_4$; pH 7.4) (Spectra/Por dialysis tubing, 5-6,000 MWCO, Spektrum, Netherlands). The dialysate is slightly turbid.

Example 15

Coupling a DNA Oligonucleotide to the Nanoparticles Prepared in Example 13

The nanoparticles prepared in Example 13 are activated with a 40-fold excess of sulfo-SIAB (sulfosuccinimidyl (4-iodoacetyl)aminobenzoate, Perbio Science Deutschland GmbH, Bonn); 7.5 mg of aminofunctionalized nanoparticles (~25 nmol) are rebuffered in TSMZ buffer, pH 7.3 (0.1 M NaCl; 0.1 M triethanolamine-HCl; 0.02 M NaOH; 0.27 mM $ZnCl_2$; 0.1% Tween 20; 1 mM $MgCl_2$) using a Centricon filter unit (MW exclusion limit at 50 000, Millipore, Eschborn) and adjusted to a concentration of about 7 mg/ml. 50 µl of a 20 mM solution of sulfo-SIAB in water are added to the particle solution and the whole is incubated at 25° C. for 15 mm. The reaction is stopped by adding 12 µl of 1 M glycine (12-fold excess) and the free sulfo-SIAB is separated off through a ready-to-use Sephadex G25 PD 10 column (Amersham Pharmacia Biotech, Freiburg). A DNA oligonucleotide having the sequence 5'-CCACGCTTGTGGGTCAACCCCCGTGG-3' (SEQ ID NO: 1), and with a thiol modification at the 5' end and a dabycl (4-(4-dimethylaminophenylazo)benzoyl) modification at the 3' end, and also a control DNA oligonucleotide, which only differs in lacking the dabcyl molecule at the 3' end of the probe, were obtained from Interactiva (Ulm). Equimolar quantities of the DNA oligonucleotide and the SIAB-activated nanoparticles are mixed and incubated at 25° C. for 3 hrs and then incubated at 4° C. overnight. The DNA oligonucleotide-coupled particles are separated off from uncoupled particles and free DNA oligonucleotide by means of an FPLC (fast performance liquid chromatography). The coupled particles are taken up in 50 mM tris-HCl, pH 7.4; 0.1% BSA at 4° C. If no target DNA is available, this molecule is present in a hairpin structure, with the ends of the molecule being directly adjacent, and a FRET takes place. The fluorescence of the nanoparticle in this connection is quenched by dabcyl.

Example 16

Coupling Anti-β-hCG Monoclonal Antibody to the Nanoparticles Prepared in Example 13

The particles prepared in Example 13 are first of all activated with a 30-fold molar excess of 2-iminothiolane (2-IT, Traut's reagent, Perbio Science Deutschland GmbH, Bonn): 2 ml (~25 nmol) of the particles prepared in Example 13 (4 mg/ml) are transferred into TSE buffer, pH 8.5 (0.04 M NaCl; 0.05 M triethanolamine-HCl; 0.04 M NaOH; 0.5 mM EDTA; 0.1% Tween 20; pH 8.5). For this, the particles are centrifuged at 3000 g for 3×15 mm and, after the excess has been decanted off, the sediment is in each case taken up in 700 µl of TSE buffer, pH 8.5. These particles are incubated, at 25° C. for 1 h, with 75 µl of 10 mM 2-IT (in TSE buffer, pH 8.5) and the reaction is then stopped with 9 µl (12-fold excess) of 1 M glycine. In order to separate off the excess of 2-IT, the mixture is once again centrifuged at 3000 g for 3×15 mm and, after decanting off, the sediment is resuspended twice in 1 ml of TSE buffer, pH 7.3 (0.1 M NaCl; 0.1 M triethanolamine-HCl; 0.02 M NaOH; 1 mM EDTA; 0.1% Tween 20; pH 7.3) and, after the third centrifugation, in 250 µl of TSE buffer, pH 7.3. At the same time, an equimolar quantity of the β-hCG-specific mouse monoclonal antibody (clone F199C1, Perkin-Elmer Life Sciences—Wallac Oy, Finland) is activated with a 40-fold excess of SMCC(N-succinimidyl-4-(N-maleimidomethyl)cyclohexane-1-carboxylate, Perbio Science Deutschland GmbH, Bonn); 750 µl of anti-β-hCG antibody (=25 nmol at a concentration of 5 mg/ml) are rebuffered in TSMZ buffer, pH 7.3 (0.1 M NaCl; 0.1 M triethanolamine-HCl; 0.02 M NaOH; 0.27 mM $ZnCl_2$; 0.1% Tween 20; 1 mM $MgCl_2$) using a Centricon filter unit (molecular weight exclusion limit at 50 000) and the solution is adjusted to a concentration of 7 mg/ml. 50 µl of a 20 mM solution of SMCC in DMF (=11 mmol) are added to the antibody solution and the mixture is incubated at 25° C. for 30 min. The reaction is stopped by adding 12 µl of 1 M glycine (12-fold excess) and the free SMCC is separated off through a ready-to-use Sephadex G25 PD 10 column (Amersham Pharmacia Biotech, Freiburg). Finally, equimolar quantities of the 2-IT-activated particle solution and the SMCC-activated antibody solution are mixed and this mixture is incubated at 25° C. for 3 hrs and then at 4° C. overnight. The antibody-coupled particles are purified from noncoupled particles and free antibody by means of gel permeation chromatography on Superdex 200 (Amersham Pharmacia Biotech, Freiburg). 0.1M MES, 0.5M NaCl, pH 6.0, is used as the running buffer. The retention time for the enlarged lid nanoparticles is about 2 hours.

Example 17

Coupling the LaPO4: $Eu^{3+}$ Nanoparticles Prepared in Example 9 to hIL-2

300 mg of the LaPO4:$Eu^{3+}$ nanoparticles (~1 µmol) prepared in Example 9 are boiled, under reflux and for 4 hours, with 2.23 g (15 mmol) of bromotrimethylsilane in 125 ml of chloroform; most of the bromotrimethylsilane excess and the intermediate which is formed are distilled off and hydrolysis subsequently takes place with a low concentration of ammonia. For this, 100 µl of 25% strength ammonia are added to 6 ml of water, with stirring then taking place at RT overnight. The particles are present in a milky emulsion and a portion of them settled out after several hours. 5 mg (=25 mmol, 106 µl) of these bromotrimethylsilane-treated nanoparticles are incubated, at 37° C. for 1 h and while shaking, with recombinant human IL-2 protein (R&D Systems, Minneapolis, Minn., USA) in 10 mM Na carbonate buffer, pH 8.5, in a molar ratio of 2:1. The excess protein is subsequently separated off by centrifuging 6 times at 3000 g for 10 min and in each case resuspending in 1 ml of 10 mM Na carbonate buffer, pH 8.5. The $LaPO_4$:$Eu^{3+}$/IL-2 conjugate is stored at 4° C.

Example 18

Homogeneous Energy Transfer Assay for Detecting β-hCG Using Antibody-coupled Nanoarticles Prepared in Example 16 and Fluorescein-coupled Antibodies as Acceptor Coupling Anti-β-hCG Antibody to Fluorescein:

The Molecular Probes Fluoreporter® FITC protein labeling kit is used, in accordance with the manufacturer's instructions, to couple the anti-β-hCG antibody (M15294, Perkin-Elmer Life Sciences, Wallac Oy, Finland) to fluorescein. 0.5 mg of the antibody is rebuffered in 0.2 M hydrogen carbonate buffer, pH 9.0, using a Centricon filter unit (molecular weight exclusion limit 50 000). A 25-fold excess of a 5 mM solution of fluorescein isothiocyanate (FITC) (dissolved in a mixture of equal volume units of DMF and 0.2 M hydrogen carbonate buffer, pH 9.0) is then added to the antibody solution and the whole is incubated at RT for 3 hrs. The excess of FITC is separated off through a ready-to-use Sephadex G25 PD 10 column (Amersham Pharmacia Biotech, Freiburg) and the antibody concentration and the fluorescein/antibody ratio are determined spectroscopically. 0.01% sodium azide and 0.1% BSA are added to the conjugate and the mixture is stored at 4° C.

Implementing the Assay:

50 μl of a β-hCG standard from a commercially available kit for measuring free β-hCG in serum (A007-101, Perkin-Elmer Life Sciences, Wallac Oy, Finland), together with 100 nmol of the nanoparticle-antibody conjugate prepared in Example 16 and 100 mmol of the fluorescein-coupled anti-β-hCG antibody, are incubated, at 25° C. for 60 min, in 200 μl of tris-HCl buffer, pH 7.4, in a UV-permeable 96-well microtiter plate (UVStar, Greiner). The two anti-β-hCG antibodies are directed against different epitopes in the β-hCG subunit. The samples are subsequently measured in a fluorescence spectrometer (from Jobin Yvon, Fluorolog 3) using the following settings: pulsed excitation with excitation wavelength: 280 nm, emission: 542 nm, slit width: 4 nm, time delay: 50 μs, repetition rate, approx. 25 Hz. The half-life of the terbium emission line can also be determined. The following settings are used for this purpose: excitation: 280 nm, emission 542 nm, slit width 5 nm; integration time: 0.1 ms. These measurements which are obtained are plotted against the β-hCG concentrations employed in order to construct a calibration curve. The body sample content of β-hCG can be measured in serum samples in an analogous manner and the concentration can be determined using the calibration curve.

Example 19

Homogeneous Competitive Energy Transfer Assay for Determining hIL-2 Using hIL-2-Coupled Nanoparticles Prepared in Example 17 and Alexa Fluor 680-Coupled anti-hIL-2Rα Chain Antibodies Coupling the anti-hIL-2Rα Chain Monoclonal Antibody to Alexa Fluor 680:

1 mg of the monoclonal antibody 7G7B6, which specifically recognizes the α chain of the human interleukin-2 receptor (hIL-2Rα chain) (ATCC, Rockville, USA), is dialyzed against PBS, adjusted to a concentration of 2 mg/ml and labeled using the Alexa Fluor 680 protein labeling kit (Molecular Probes Europe BV, Netherlands) in accordance with the manufacturer's instructions. 0.1 M Na bicarbonate buffer, pH 8.3, is used as the reaction buffer and the mixture is incubated at RT for 1 h. The coupled antibody is purified using a column contained in the kit, with PBS buffer containing 0.2 mM Na azide being employed as the elution buffer. In order to determine the protein concentration of the coupled antibody, the absorption (A) is measured at 280 and 679 nm in a 1 cm cuvette and the calculation uses the following formula:

$$M = \frac{(A_{280} - (A_{679} \times 0.05)) \times \text{dilution factor}}{203000}$$

where 203 000 cm$^{-1}$M$^{-1}$ is the molar extinction coefficient of an IgG and 0.05 is the factor for correcting the absorption of the dye at 280 nm. The concentration of the coupled antibody is 1.27 and is adjusted with PBS; 0.2 mM Na azide to 1 mg/ml (~6.5 μM); the antibody solution is then stored at 4° C. The efficiency of the labeling is calculated as follows:

$$\text{mol of dye per mol of antibody} = \frac{A_{679} \times \text{dilution factor}}{18000 \times \text{protein concentration } M}$$

where 184 000 cm$^{-1}$M$^{-1}$ is the molar extinction coefficient of the Alexa Fluor 680 dye at 670 nm. The ratio of the antibody-dye conjugate is 3.2.

Implementing the Assay:

The necessary dilutions of the different components are performed in 50 mM TSA buffer (50 mM tris-HCl, pH 7.75; 0.9% NaCl; 0.05% NaN$_3$). 40 wells of a UV-permeable microtiter plate (UVStar, Greiner) are first of all incubated, at RT for 1 h, with a 0.5% strength solution of BSA in order to saturate nonspecific binding sites and then loaded with a mixture consisting of nanoparticles prepared in Example 17 (LaPO$_4$: Eu$^{3+}$/IL-2 conjugate), Alexa Fluor 680-labeled anti-hIL-2Rα chain antibody and recombinant hIL-2sRα protein (human IL-2 soluble alpha receptor, R&D Systems, Minneapolis, Minn.) at a final concentration of 40 nM in each case. Unlabeled hIL-2 protein is added to 20 of the wells at different concentrations, while a protein which is irrelevant to this assay is added to the other 20 wells. The concentration is in each case increased by 50 nM such that a concentration series of 0-950 nM is tested. The final volume of the reaction is in each case 200 μl. The plate is incubated at RT for 45 mm in the dark on a shaker. The signals are read using a Wallac 1420 Victor™ multilabel counter (Perkin-Elmer Life Sciences Wallac Oy, Finland) and employing the following settings: excitation: 340 nm, emission: 665 nm, time delay: 50 μs, time window: 200 μs and cycling time: 1000 μs. A duplicate determination is carried out for each value and a correction is made for nonspecific binding sites using the results obtained with the irrelevant protein. The measured values are plotted in a graph against the protein concentration employed and result in a calibration curve which can be used to determine the concentrations of human interleukin-2 which are measured, in an analogous manner, in human body samples.

Example 20

Quantitative PCR Determination of Bacterial DNA by Means of an Intramolecular Energy Transfer Using the Nanoparticles Prepared in Example 15

The primers and the probe for the quantitative DNA determination were chosen specifically for the *Mycobacterium tuberculosis* RNA polymerase gene and were prepared at Interactiva (Ulm). The primers have the following sequences:

```
forward:   5'-GGCCGGTGGTCGCCGCG-3',    (SEQ ID NO: 2)

backward:  5'-ACGTGACAGACCGCCGGGC-3'.  (SEQ ID NO: 3)
```

Assay for Quantitatively Determining Bacterial DNA 50 nM of the nanoparticles prepared in Example 15 (Dabcyl-oligonucleotide-coupled), as probe, in each case 500 nM of the two primers, 2 U of Amplitaq Gold DNA polymerase (Perkin-Elmer), 250 µM of dATP, 250 µM of dCTP, 250 µM of dGTP, 500 µM of dUTP, 4 mM of MgCl2, 50 mM of KCl and 10 mM of tris-HCl, pH 8.0, are mixed for the 50 µL PCR reactions. As the DNA template, genomic *M. tuberculosis* DNA is amplified with the same primers and cloned into a plasmid using the Invitrogen Zero Blunt TOPO PCR Cloning Kit (Invitrogen BV/NOVEX, Netherlands). In order to construct a standard curve, 5 different concentrations, of from 1 µg to 100 ng, of the DNA plasmid are used, as is a reaction without DNA template. 30 reactions are prepared for each concentration, such that, starting from the 15$^{th}$ cycle, a sample can be withdrawn, for measuring in a spectrometer, after each further cycle. The reaction volume is 50 µL and the amplification is carried out on a Thermocycler (PCR system 2400, Perkin-Elmer) under the following reaction conditions: 10 min, 95° C.; 15-45 cycles of 30 s at 95° C., 45 s at 56° C. and 30 s at 72° C. The samples are measured in a fluorescence spectrometer (from Jobin Yvon, Fluorolog 3) using the following settings: pulsed excitation with excitation wavelength: 280 µm, emission: 542 nm, slit width: 4 nm, time delay: 50 µs, repetition rate approx. 25 Hz. It is also possible to determine the half-life of the terbium emission line. The following settings are used for this purpose: excitation: 280 nm, emission 542 nm, slit width 5 nm; integration time: 0.1 ms. No intramolecular FRET takes place between the nanoparticle and the dabcyl during hybridization of the probe to the target DNA. The Th fluorescence of the nanoparticle therefore becomes stronger, as compared with the control without template, as the concentration of the target DNA increases; at the same time, the half-life of the fluorescence lifetime of the nanoparticle becomes longer as compared with the control without template DNA. These differences in the two parameters can be plotted against the number of cycles in order to construct a calibration curve for each DNA template concentration.

The invention claimed is:

1. An assay kit for carrying out an assay method based on a resonance energy transfer (RET), said assay kit comprising:
   a) a first molecule group A which is labeled with at least one energy donor (donor), and
   b) at least a second molecule group B which is labeled with at least one energy acceptor (acceptor),
   wherein the donor comprises a molecule or particle which can be energetically excited by an external radiation source and is capable of fluorescing,
   the acceptor comprises a molecule or particle which can be excited by energy transfer by way of the donor, with partial or complete quenching of the donor fluorescence, and
   donor and/or acceptor comprise luminescent inorganic doped nanoparticles (lid nanoparticles) which have a breadth of >50 nanometers and which, after an energetic excitation, emit electromagnetic radiation with a Stokes shift or an anti-Stokes shift.

2. The assay kit as claimed in claim 1, wherein the acceptor is also capable of fluorescing.

3. The assay kit as claimed in claim 1, wherein the acceptor relaxes in a radiationless manner.

4. The assay kit as claimed in claim 1, wherein the RET is a fluorescence resonance energy transfer (FRET).

5. The assay kit as claimed in claim 1, wherein the RET is a Förster transfer or a transfer involving higher multiple orders.

6. The assay kit as claimed in claim 1, wherein the RET is a migration of charges or excitons.

7. The assay kit as claimed in claim 1, wherein the RET can be qualitatively and/or quantitatively recorded by a time-resolved or continuous measurement of a change in the luminescence properties.

8. The assay kit as claimed in claim 7, wherein the RET is qualitatively and/or quantitatively recorded by a time-resolved or continuous measurement of a change in an intensity of the fluorescent light, a change in the spectrum of the fluorescent light or a change in the decay time of the lid nanoparticles and/or of other donors and/or acceptors.

9. The assay kit as claimed in claim 7, wherein the RET is qualitatively and/or quantitatively recorded by a time-resolved or continuous measurement of a change in an intensity of the fluorescent light, a change in the spectrum of the fluorescent light or a change in the decay time of a chromophoric donor/acceptor.

10. The assay kit as claimed in claim 1, wherein either the donor or acceptor comprises lid nanoparticles which have a long fluorescence decay time and the other one of the donor or acceptor either also comprises lid nanoparticles whose fluorescence decay time is shorter than that of the other lid nanoparticles or comprises a molecular organic chromophore.

11. The assay kit as claimed in claim 10, wherein either the donor or acceptor comprises lid nanoparticles which exhibit a half life of more than 5 ns.

12. The assay kit as claimed in claim 11, wherein either the donor or acceptor comprises lid nanoparticles which exhibit a half life between 1 μs and 50 ms.

13. The assay kit as claimed in claim 12, wherein either the donor or acceptor comprises lid nanoparticles exhibit a half life between 100 μs and 10 ms.

14. The assay kit as claimed in claim 1, wherein the lid nanoparticles have a breadth in the range of from 1 nm to 50 nm.

15. The assay kit as claimed in claim 14, wherein the lid nanoparticles have a breadth in the range of from 1 nm to less than 20 nm.

16. The assay kit as claimed in claim 15, wherein the lid nanoparticles have a breadth in the range of from 2 nm to 10 nm.

17. The assay kit as claimed in claim 1, wherein the lid nanoparticles exhibit a needle-shaped morphology having a breadth in the range from 3 nm to 50 nm and a length in the range from 20 nm to 5 μm.

18. The assay kit as claimed in one of claim 17, wherein the lid nanoparticles exhibit a needle-shaped morphology having a breadth in the range from 3 nm to 20 nm and/or a length in the range from 20 nm to 500 nm.

19. The assay kit as claimed in claim 1, wherein a host material of the lid nanoparticles comprises compounds of the type XY, where X is a cation consisting of one or more elements of main groups 1a, 2a, 3a or 4a, of the subgroups 2b, 3b, 4b, 5b, 6b or 7b, or of the lanthanides, of the Periodic Table, and Y is either a polyatomic anion consisting of one or more element(s) of the main groups 3a, 4a or 5a, or of the subgroups 3b, 4b, 5b, 6b, 7b and/or 8b, and also element(s) of the main groups 6a and/or 7, or else is a monoatomic anion from the main group 5a, 6a or 7a of the Periodic Table.

20. The assay kit as claimed claim 1, wherein a host material of the lid nanoparticles comprises at least one compound selected from the group consisting of sulfides, selenides, sulfoselenides, oxysulfides, borates, aluminates, gallates, silicates, germanates, phosphates, halophosphates, oxides, arsenates, vanadates, niobates, tantalates, sulfates, tungstates, molybdates, alkali metal halides and other halides, and nitrides.

21. The assay kit as claimed in claim 1, wherein the lid nanoparticles comprise a doping material comprising one or more elements selected from the group consisting of elements of the main groups 1a or 2a, or Al, Cr, Tl, Mn, Ag, Cu, As, Nb, Nd, Ni, Ti, In, Sb, Ga, Si, Pb, Bi, Zn or Co, and/or elements of the lanthanides.

22. The assay kit as claimed in claim 21, wherein the doping material comprises a combination of two or more of said elements, in different relative concentrations to each other.

23. The assay kit as claimed in claim 1, wherein the lid nanoparticles comprise a doping material in a concentration of the doping material in a host lattice of between $10^{-5}$ mol % and 50 mol %.

24. The assay kit as claimed in claim 23, wherein the concentration of the doping material in the host lattice is between 0.01 mol % and 30 mol %.

25. The assay kit as claimed in claim 24, wherein the concentration of the doping material in the host lattice is between 0.1 mol % and 20 mol %.

26. The assay kit as claimed in claim 1, wherein the lid nanoparticles comprise a material selected from the group consisting of $YVO_4$:Eu, $YVO_4$:Sm, $YVO_4$:Dy, $LaPO_4$:Eu, $LaPO_4$:Ce, $LaPO_4$:Ce,Tb, $LaPO_4$:Ce,Dy, $LaPO_4$:Ce,Nd, ZnS:Th, $ZnS:TbF_3$, ZnS:Eu $ZnS:EuF_3$, $Y_2O_3$:Eu, $Y_2O_2S$:Eu, $Y_2SiO_5$:Eu, $SiO_2$:Dy, $SiO_2$:Al, $Y_2O_3$:Tb, CdS:Mn, ZnS:Tb, ZnS:Ag and ZnS:Cu.

27. The assay kit as claimed in claim 1, wherein the lid nanoparticles comprise a material in which the host lattice has a cubic structure.

28. The assay kit as claimed in claim 1, wherein the lid nanoparticles comprise a material selected from the group consisting of $MgF_2$:Mn, ZnS:Mn, ZnS:Ag, ZnS:Cu, $CaSiO_3$:Ln, CaS:Ln, CaO:Ln, ZnS:Ln, $Y_2O_3$:Ln, and $MgF_2$:Ln (Ln=lanthanides).

29. The assay kit as claimed in claim 1, wherein the donor and/or the acceptor comprise lid nanoparticles which, after energetic excitation with electromagnetic radiation with wavelengths in the range of infrared light, of visible light, of UV, of X-ray light or of γ-radiation, or particle radiation emit electromagnetic radiation with a Stokes shift or anti-Stokes shift.

30. The assay kit as claimed in claim 1, wherein the donor and/or the acceptor comprise lid nanoparticles which, after energetic excitation with electromagnetic radiation with wavelengths in the range of electron radiation, emit electromagnetic radiation with a Stokes shift or anti-Stokes shift.

31. The assay kit as claimed in claim 1, wherein the donor comprises lid nanoparticles and the acceptor comprises a conducting material.

32. The assay kit as claimed in claim 31, wherein the conducting material is a metal, a conducting oxide, or a conducting polymer.

33. The assay kit as claimed in claim 32, wherein the conducting material is a metal selected from the group consisting of gold, silver and platinum; the conducting oxide is indium tin oxide (ITO); and the conducting polymer is present in particulate form as nanoparticles or microparticles or as a planar, optionally structured, surface.

34. The assay kit as claimed in claim 1, which is capable of use in a homogeneous assay without any washing or separating steps.

35. The assay kit as claimed in claim 1, which is capable of use in a homogeneous immunoassay detecting at least one analyte in a sample.

36. The assay kit as claimed in claim 35, wherein the at least one analyte is selected from the group consisting of at least one monoclonal or polyclonal antibody, protein, peptide, oligonucleotide, nucleic acid, oligosaccharide, polysaccharide, hapten and low molecular weight synthetic or natural antigen; and/or the sample comprises at least one member selected from the group consisting of smears, sputum, organ punctate, biopsies, secretions, spinal fluid, bile, blood, lymph fluid, urine and feces.

37. The assay kit as claimed in claim 1, wherein a surface of the lid nanoparticle(s) is prepared such that affinity molecules can be coupled to it.

38. The assay kit as claimed in claim 37, wherein the surface of the lid nanoparticles is chemically modified and/or exhibits reactive groups and/or covalently or noncovalently bound connecting molecules, with the bound connecting molecules being able, for their part, to exhibit reactive groups.

39. The assay kit as claimed in claim 38, wherein the reactive groups are selected from the group consisting of amino groups, carboxylic acid groups, thiols, thioethers, disulfides, imidazoles, guanidines, hydroxyl groups, indoles, vicinal diols, aldehydes, alpha-haloacetyl groups, N-maleimides, mercurides, aryl halides, acid anhydrides, isocyanates, isothiocyanates, sulfonyl halides, imidoesters, diazoacetates, diazonium salts, 1,2-diketones, alpha-beta-unsaturated carbonyl compounds, phosphonic acids, phosphoric acid esters, sulfonic acids and azolides, and derivatives of said reactive groups.

40. The assay kit as claimed in claim 39, wherein the connecting molecules are selected from the group consisting of nucleic acid molecules, phosphonic acid derivatives, ethylene glycol, primary alcohols, amine derivatives, polymers or copolymers, polymerizable coupling agents, silica shells and catenate molecules having a polarity which is opposite to that of the surface of the lid nanoparticles.

41. The assay kit as claimed in claim 40, wherein the polymerizable coupling agents are selected from the group consisting of diacetylenes, styrenebutadienes, vinyl acetate, acrylates, acrylamides, vinyls, styrenes, silicone oxides, boron oxides, phosphorus oxides, borates, pyrroles, polypyrroles and phosphates, and also polymers of at least some of said polymerizable coupling agents.

42. The assay kit as claimed in claim 37, wherein the affinity molecules are selected from the group consisting of proteins, peptides, oligonucleotides or other nucleic acid molecules or nucleic acid-like molecules, oligosaccharides or polysaccharides, haptens, and low molecular weight synthetic natural antigens or epitopes.

43. The assay kit as claimed in claim 42, wherein the nucleic acid-like molecules are PNAs or morpholinos; and/or the haptens are biotin or digoxin.

44. The assay kit as claimed in claim 37, wherein the affinity molecules are able to interact with target molecules.

45. The assay kit as claimed in claim 44, wherein the target molecule is an enzyme, an antibody, a nucleic acid-binding molecule, a nucleic acid, a polynucleotide or a morpholino.

46. The assay kit as claimed in claim 45, wherein the enzyme is endonuclease, protease, kinase or phosphatase or an amino acid- or nucleic acid-modifying or cleaving enzyme.

47. The assay kit as claimed in claim 46, wherein an interaction of the affinity molecule with the target molecule results in a change in a spatial separation of molecule groups A and B.

48. The assay kit as claimed in claim 1, wherein the molecule groups A and B are constituents of one and the same molecule.

49. The assay kit as claimed in claim 1, wherein the molecule groups A and B are able to couple to the same affinity molecule.

50. The assay kit as claimed in claim 1, which is used for quantifying nucleic acids.

51. The assay kit as claimed in claim 1, wherein the molecule groups A and B are constituents of different molecules.

52. The assay kit as claimed in claim 51, wherein the molecule groups A and B are in each case coupled to their own affinity molecules.

53. The assay kit as claimed in claim 52, wherein the affinity molecules which are assigned to molecule groups A and B are able to interact specifically with the same target molecule.

54. The assay kit as claimed in claim 53, wherein an interaction of the affinity molecules which are assigned to molecule groups A and B with the common target molecule or with each other result in a change in the spatial separation of molecule groups A and B.

55. The assay kit as claimed in claim 52, wherein the affinity molecules which are assigned to molecule groups A and B are able to interact specifically with each other.

56. The assay kit as claimed in claim 1, wherein the lid nanoparticles comprise a material selected from the group consisting of LiI:Eu; NaI:Tl; CsI:Tl; CsI:Na; Lif:Mg; LiF:Mg,Ti; LiF:Mg,Na; KMgF$_3$:Mn; Al$_2$O$_3$:Eu; BaFCl:Eu; BaFCl:Sm; BaFBr:Eu; BaFCl$_{0.5}$Br$_{0.5}$:Sm; BaY$_2$F$_8$:A (A=Pr, Tm, Er or Ce); BaSi$_2$O$_5$:Pb; BaMg$_2$Al$_{16}$O$_{27}$:Eu; BaMgAl$_{14}$O$_{23}$:Eu; BaMgAl$_{10}$O$_{17}$:Eu; BaMgAl$_2$O$_3$:Eu; Ba$_2$P$_2$O$_7$:Ti; (Ba,Zn or Mg)$_3$Si$_2$O$_7$:Pb; Ce(Mg or Ba)Al$_{11}$O$_{19}$; Ce$_{0.65}$Tb$_{0.35}$MgAl$_{11}$O$_{19}$:(Ce or Tb); MgAl$_{11}$O$_{19}$:(Ce or Tb); MgF$_2$:Mn; MgS:Eu; MgS:Ce; MgS:Sm; MgS:(Sm or Ce); (Mg or Ca)S:Eu; MgSiO$_3$:Mn; 3.5MgO.0.5MgF$_2$.GeO$_2$:Mn; MgWO$_4$: Sm; MgWO$_4$:Pb, 6MgO.As$_2$O$_5$:Mn; (Zn or Mg)F$_2$:Mn; (Zn$_4$Be)SO$_4$:Mn; Zn$_2$SiO$_4$:Mn; Zn$_2$SiO$_4$:Mn,As; ZnO:Zn; ZnO:Zn, Si,Ga; Zn$_3$(PO$_4$)$_2$Mn; ZnS:A (A=Ag, Al or Cu); (Zn or Cd)S:A (A=Cu, Al, Ag or Ni); CdBO$_4$:Mn; CaF$_2$:Mn; CaF$_2$:Dy; CaS:A (A=lanthanides or Bi); (Ca or Sr)S:Bi; CaWO$_4$:Pb; CaWO$_4$:Sm; CaSO$_4$:A (A=Mn or lanthanides); 3Ca$_3$(PO$_4$)$_2$.Ca(F or Cl)$_2$:Sb,M$_n$; CaSiO$_3$:(Mn or Pb);

$Ca_2Al_2Si_2O_7$:Ce; (Ca or Mg)$SiO_3$:Ce; (Ca or Mg)$SiO_3$:Ti; 2SrO.6($B_2O_3$).$SrF_2$:Eu; $3Sr_3(PO_4)_2.CaCl_2$:Eu; $A_3(PO_4)_2.ACl_2$:Eu (A=Sr, Ca or Ba); (Sr or Mg)$_2P_2O_7$:Eu; (Sr or Mg)$_3(PO_4)_2$:Sn; SrS:Ce; SrS:Sm,Ce; SrS:Sm; SrS:Eu; SrS:Eu,Sm; SrS:(Cu or Ag); $Sr_2P_2O_7$:Sn; $Sr_2P_2O_7$:Eu; $Sr_4Al_{14}O_{25}$:Eu; $SrGa_2S_4$A (A=lanthanides or Pb); $SrGa_2S_4$:Pb; $Sr_3Gd_2Si_6O_{18}$:Pb,Mn; $YF_3$:Yb,Er; $YF_3$:Ln (Ln=lanthanides); $YLiF_4$:Ln (Ln=lanthanides); $Y_3Al_5O12$:Ln (Lu=lanthanides); $YAl_3(BO_4)_3$:(Nd or Yb); (Y or Ga)$BO_3$:Eu; (Y or Gd)$BO_3$:Eu; $Y_2Al_3Ga_2O_{12}$:Tb; $Y_2SiO_5$:Ln (Ln=lanthanides); $Y_2O_3$:Ln (Ln=lanthanides); $Y_2O_2S$:Ln (Lu=lanthanides); $YVO_4$:A (A=lanthanides or In); Y(P,V)$O_4$:Eu; $YTaO_4$:Nb; $YAlO_3$:A (A=Pr, Tm, Er or Ce); YOCl:(Yb or Er); $LnPO_4$: (LnCe or Tb=lanthanides or mixtures of lanthanides); $LuVO_4$:Eu; $GdVO_4$:Eu; $Gd_2O_2S$:Tb; $GdMgB_5O_{10}$:(Ce or Tb); LaOBr:Tb; $La_2O_2S$:Tb; $LaF_3$(Nd or Ce); $BaYb_2F_8$:Eu; $NaYF_4$:(Yb or Er); $NaGdF_4$:(Yb or Er); $NaLaF_4$:(Yb or Er); $LaF_3$:Yb, Er or Tm); $BaYF_5$:(Yb or Er); $Ga_2O_3$:Dy; GaN:A (A=Pr, Eu, Er or Tm); $Bi_4Ge_3O_{12}$; $LiNbO_3$:(Nd or Yb); $LiNbO_3$:Er; $LiCaAlF_6$:Ce; $LiSrAlF_6$:Ce; $LiLuF_4$:A (A=Pr, Tm, Er or Ce); $Li_2B_4O_7$:Mn, and $SiO_x$:(Er or Al) ($0 \leq x \leq 2$).

57. A method for detecting a target molecule, comprising the steps of:
   a) providing an assay kit as claimed in claim 1,
      wherein, in the assay kit, the molecule groups A and B are constituents of one and the same molecule and couple to the same affinity molecule, which is capable of interacting with a specific target molecule, and such an interaction brings about a change in the separation between the molecule groups A and B,
   b) adding a sample containing the target molecule to the assay kit,
   c) exciting the assay kit containing the sample with a source of electromagnetic or particulate radiation, and
   d) measuring the electromagnetic radiation emitted by the assay kit containing the sample,
      wherein the intensity or the spectrum of the emitted electromagnetic radiation, or the chronological course of the emission of the electromagnetic radiation, is a measure of the quantity of target molecule in the sample.

58. A method for detecting a target molecule, comprising the steps of:
   a) providing an assay kit as claimed in claim 1,
      wherein the molecule groups A and B are constituents of different molecules, and
      the affinity molecules which are assigned to molecule groups A and B are capable of specifically interacting with one and the same target molecule, or
      the affinity molecules which are assigned to molecule groups A and B are capable of specifically interacting with each other,
      and in both cases an interaction brings about a change in the separation between molecule groups A and B,
   b) adding a sample containing the target molecule to the assay kit,
   c) exciting the assay kit containing the sample with a source of electromagnetic or particulate radiation, and
   d) measuring the electromagnetic radiation emitted by the assay kit containing the sample,
      where the intensity or the spectrum of the emitted electromagnetic radiation, or the chronological course of the emission of the electromagnetic radiation, is a measure of the quantity of target molecule in the sample.

* * * * *

UNITED STATES PATENT AND TRADEMARK OFFICE
CERTIFICATE OF CORRECTION

| | | |
|---|---|---|
| PATENT NO. | : 7,410,810 B2 | Page 1 of 1 |
| APPLICATION NO. | : 10/494390 | |
| DATED | : August 12, 2008 | |
| INVENTOR(S) | : Bohmann et al. | |

It is certified that error appears in the above-identified patent and that said Letters Patent is hereby corrected as shown below:

Abstract (57), line 63, "$\leqq$" should read -- $\leq$ --

Column 25, line 17, ">" should read -- $\leq$ --

Column 29, line 22, "$(0 \leqq x \leqq 2)$." should read -- $(0 \leq x \leq 2)$. --

Signed and Sealed this

Tenth Day of August, 2010

David J. Kappos
*Director of the United States Patent and Trademark Office*